(12) United States Patent
Fukunaga et al.

(10) Patent No.: US 10,709,688 B2
(45) Date of Patent: Jul. 14, 2020

(54) AGENT FOR TREATING SYNUCLEINOPATHY

(71) Applicants: TOHOKU UNIVERSITY, Aoba-ku, Sendai-shi, Miyagi (JP); NATIONAL UNIVERSITY CORPORATION OKAYAMA UNIVERSITY, Kita-ku, Okayama-shi, Okayama (JP)

(72) Inventors: Kohji Fukunaga, Miyagi (JP); Hiroyuki Miyachi, Okayama (JP); Hiroaki Ishida, Tokyo (JP); Shintaro Ban, Tokyo (JP)

(73) Assignees: Tohoku University, Miyagi (JP); National University Corporation Okayama University, Okayama (JP)

( * ) Notice: Subject to any disclaimer, the term of this patent is extended or adjusted under 35 U.S.C. 154(b) by 0 days.

(21) Appl. No.: 16/089,536

(22) PCT Filed: Mar. 31, 2017

(86) PCT No.: PCT/JP2017/013742
§ 371 (c)(1),
(2) Date: Sep. 28, 2018

(87) PCT Pub. No.: WO2017/171053
PCT Pub. Date: Oct. 5, 2017

(65) Prior Publication Data
US 2019/0125726 A1     May 2, 2019

(30) Foreign Application Priority Data
Mar. 31, 2016    (JP) ................ 2016-073115

(51) Int. Cl.
| | | |
|---|---|---|
| A61K 31/415 | (2006.01) | |
| C07D 231/12 | (2006.01) | |
| A61P 25/28 | (2006.01) | |
| A61P 25/16 | (2006.01) | |
| A61K 9/00 | (2006.01) | |

(52) U.S. Cl.
CPC ............ *A61K 31/415* (2013.01); *A61P 25/16* (2018.01); *A61P 25/28* (2018.01); *C07D 231/12* (2013.01); *A61K 9/0053* (2013.01)

(58) Field of Classification Search
CPC ..... A61K 31/415; C07D 231/12; A61P 25/28; A61P 25/16
USPC ........................................ 514/406
See application file for complete search history.

(56) References Cited

FOREIGN PATENT DOCUMENTS

| CN | 101838239 A | 9/2010 |
|---|---|---|
| WO | WO 2010/000372 A2 | 1/2010 |

OTHER PUBLICATIONS

Beniyama et al. Bioorganic & Medicinal Chemistry Letters (2013), 23(6), 1662-1666.*
International Search Report dated May 23, 2017, in PCT/JP2017/013742.
Beniyama et al., "Structure-guided design, synthesis and in vitro evaluation of a series of pyrazole-based fatty acid binding protein (FABP) 3 ligands," Bioorganic & Medicinal Chemistry 23:1662-1666.
Hasim et al., "A Glutathione-independent Glyoxalase of the DJ-1 Superfamily Plays an Important Role in Managing Metabolically Generated Methylglyoxal in *Candida albicans*," The Journal Chemistry, Jan. 17, 2014, 289(3):1662-1674.
Liu et al., "New aromatic substituted pyrazoles as selective inhibitors of human adipocyte fatty acid-binding protein," Bioorganic & Medicinal Chemistry Letters, 2011, 21:2949-2952.
Onozato et al., "Shibosan Ketsugo Tanpakushitsu FABP3 no alpha-synuclein Gyoshutai Keisei eno Kan'yo," The Pharmaceutical Society of Japan Tohoku Shibu Taikai Koen Yoshishu, 2013, 52:47.
Paumier et al., Intrastriatal injection of pre-formed mouse alpha-synuclein fibrils into rats triggers alpha-synuclein pathology and bilateral nigrostriatal degeneration, Neurobiol. Dis., Oct. 2015, 82:185-199.
Supplementary European Search Report dated Oct. 28, 2019, in EP 17775584.0.
Cheng et al., "Development of FABP3 ligands that inhibit arachidonic acid-induced α-synuclein oligomerization," Brain Research, Nov. 26, 2018, 1707:190-197.
Fukunaga et al., "Fatty acid-binding protein 3 (FABP3) is critical for alpha-synuclein oligomerization in Parkinson disease," Journal of Neurochemistry, Aug. 1, 2015, 134(Suppl):129-130.
Matsuo et al., "Inhibition of MPTP-induced α-synuclein oligomerization by fatty acid-binding protein 3 ligand in MPTP-treated mice," Neuropharmacology, May 15, 2019, 150:164-174.
Shioda et al., "FABP3 Protein Promotes α-Synuclein Oligomerization Associated with 1-Methyl-1,2,3,6-tetrahydropiridine-induced Neurotoxicity," The Journal of Biological Chemistry, Jul. 4, 2014, 289(27):18957-18965.
Tan et al., "Interaction kinetics of liposome-incorporated unsaturated fatty acids with fatty acid-binding protein 3 by surface plasmon resonance," Bioorganic & Medicinal Chemistry, Feb. 13, 2014, 22(6):1804-1808.
Office Action dated Apr. 17, 2020 in JP 2018-509686.
Onosato et al,. "C-6 Fatty Binding Protein Involves α-Synuclein Aggregate Formation of FABP3," Abstracts of the 52nd Annual Meeting of the Pharmaceutical Society of Japan, Tohoku branch, Oct. 20, 2013, C-6:46, with English translation.
Wakabayashi, Koichi, Clinical Neurology, 2013, 53(8):609-617, with partial English translation of indicated portion.

* cited by examiner

*Primary Examiner* — Kahsay Habte
(74) *Attorney, Agent, or Firm* — Foley & Lardner LLP

(57) ABSTRACT

This invention provides a pharmaceutical composition for treating or preventing synucleinopathy comprising a compound represented by formula (I), or a pharmaceutically acceptable salt thereof.

24 Claims, 12 Drawing Sheets
Specification includes a Sequence Listing.

Figure 14

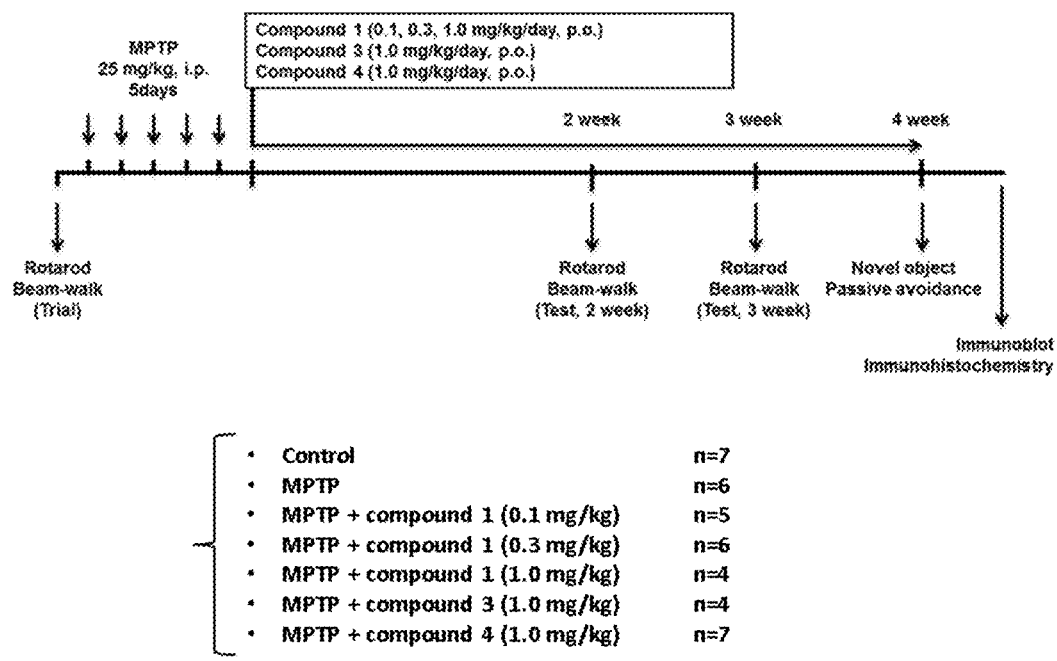

Figure 15

```
<GST-FABP3>
GGATCCATGGCGGACGCCTTTGTCGGTACCTGGAAGCTAGTGGACAGCAAGAATTTTGAT
GACTACATGAAGTCACTCGGTGTGGGCTTTGCCACCAGGCAGGTGGCTAGCATGACCAAG
CCTACTACCATCATCGAGAAGAACGGGGATACTATCACCATAAAGACACAAAGTACCTTC
AAGAACACAGAGATCAACTTTCAGCTGGGAATAGAGTTCGACGAGGTGACAGCAGATGAC
CGGAAGGTCAAGTCACTGGTGACGCTGGACGGAGGCAAACTCATCCATGTGCAGAAGTGG
AACGGGCAGGAGACAACACTAACTAGGGAGCTAGTTGACGGGAAACTCATCCTGACTCTC
ACTCATGGCAGTGTGGTGAGCACTCGGACTTATGAGAAGGAGGCGTGAGAATTC
<GST-FABP4>
GGATCCATGTGTGATGCCTTTGTGGGAACCTGGAAGCTTGTCTCCAGTGAAAACTTCGAT
GATTACATGAAAGAAGTGGGAGTGGGCTTTGCCACAAGGAAAGTGGCAGGCATGGCCAAG
CCCAACATGATCATCAGCGTAAATGGGGATTTGGTCACCATCCGGTCAGAGAGTACTTTTA
AAAACACCGAGATTTCCTTCAAACTGGGCGTGGAATTCGATGAAATCACCGCAGACGACA
GGAAGGTGAAGAGCATCATAACCCTAGATGGCGGGGCCCTGGTGCAGGTGCAGAAGTGG
GATGGAAAGTCGACCACAATAAAGAGAAAACGAGATGGTGACAAGCTGGTGGTGGAATGT
GTTATGAAAGGCGTGACTTCCACAAGAGTTTATGAAAGGGCATGAGAATTC
```

AGENT FOR TREATING SYNUCLEINOPATHY

CROSS-REFERENCE TO RELATED APPLICATIONS

This application is a National Stage application of PCT/JP2017/013742, filed Mar. 31, 2017, which claims priority from Japanese application JP 2016-073115, filed Mar. 31, 2016.

TECHNICAL FIELD

The present invention relates to a therapeutic agent or a prophylactic agent of synucleinopathy. The present invention further relates to a pharmaceutical composition for treating or preventing synucleinopathy comprising a derivative of 1,3,5-triphenylpyrazole, and to a method for treating or preventing synucleinopathy using said compound.

BACKGROUND ART

α-Synuclein is a protein consisting of 140 residues of amino acids encoded by the SNCA gene, and it is expressed richly in the presynaptic terminal in the brain. Synucleinopathies are a group of neurodegenerative diseases characterized by the abnormal accumulation of α-synuclein, and known examples include an accumulation in the Lewy bodies/neurites in the Lewy bodies dementia, and an accumulation of glial cytoplasmic inclusion of multiple system atrophy. It has been reported that a polyunsaturated fatty acid is involved in the oligomerization of α-synuclein (Non-patent documents 1 and 2). These days, in this country where the society is aging rapidly, the number of patients suffering a disease that can be categorized as synucleinopathy is considerably increasing.

Fatty Acid Binding Protein (FABP) is a cytoplasm-type protein having a low molecular weight (14 to 15 kDa), and it shows tissue specific expression. FABP holds as its ligand, a middle chain to long chain fatty acid, and is believed to be involved in the retention of homeostasis or transduction of signals in a lipid metabolism. FABP is known to have multiple subtypes with mutually analogous molecule structures. FABP3 is expressed in the heart, and although its function is not fully elucidated, it is believed to be involved in the lipid homeostasis such as the incorporation of lipid, and the transportation to β-oxidation in mitochondria. There has been a report of a compound having an inhibitory activity against FABP3 (Non-patent Document 2). There has also been a report that FABP3 accelerates the α-synuclein aggregation (Non-patent Document 1).

In the Parkinson's disease, the α-synuclein aggregate (inclusion) appears in the substantia nigra dopamine neurons, and in the dementia with Lewy bodies, it appears in a diffuse state in the cerebral cortex. When the filamentous synuclein is injected into a rat corpus striatum, the aggregate is propagated to the cerebral cortex as well as the substantia nigra, and forms a synuclein inclusion in the nerve cell (Non-patent Document 3).

CITATION LIST

Non Patent Literature

[Non-patent Document 1] *J. Biol. Chem.* 289 (2014) 1662-1666

[Non-patent Document 2] *Bioorg. Med. Chem. Lett.* 23 (2013) 1662-1666

[Non-patent Document 3] *Neurobiology of Disease* 2015; 82: 185-199

SUMMARY OF INVENTION

Technical Problem

No therapeutic or prophylactic method is established that can provide a sufficient effect against the neurodegenerative disease classified as synucleinopathy, and a need exists for a new therapeutic or prophylactic agent.

In one aspect, the object of the present invention is to provide a pharmaceutical composition for use in treating or preventing synucleinopathy. An additional object of the present invention is to provide a therapeutic or prophylactic method of synucleinopathy using a specific derivative of 1,3,5-triphenylpyrazole.

Solution to Problem

The present inventors performed extensive studies to achieve the above objects, and found that the derivative of 1,3,5-triphenylpyrazole has beneficial effects, such as suppressing the aggregation of α-synuclein, considerably suppressing the propagation of α-synuclein aggregates by a FABP3 ligand, and ameliorating the motor dysfunction and cognitive dysfunction, and thereby completed the present invention. The disclosure of this specification encompasses the descriptions of the inventions of [1] to [20] described below.

[1] A pharmaceutical composition for treating or preventing synucleinopathy comprising a compound represented by formula (I):

[Formula 1]

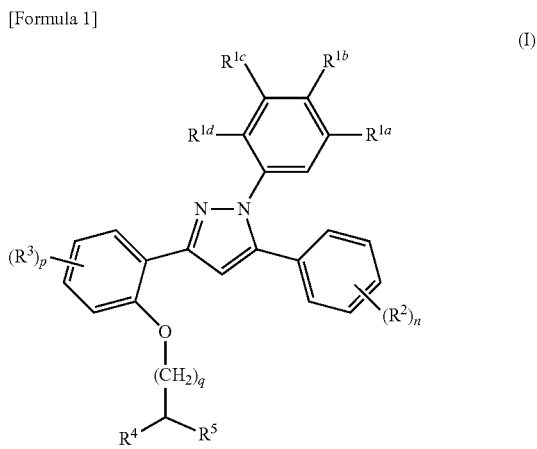

(I)

wherein, $R^{1a}$, $R^{1b}$ and $R^{1c}$ are independently selected from a hydrogen atom, $C_{1-6}$ alkyl, $C_{1-6}$ alkoxy, and a halogen atom;

$R^{1d}$ is a hydrogen atom, or a halogen atom;

$R^2$ and $R^3$ are independently selected from $C_{1-6}$ alkyl, and a halogen atom;

$R^4$ is selected from a hydrogen atom, and $C_{1-6}$ alkyl;

$R^5$ is selected from $COOR^6$, $CH_2OH$, and 1-tetrazolyl;

$R^6$ is selected from a hydrogen atom, and $C_{1-6}$ alkyl;

n is an integer selected from 0 to 5;

p is an integer selected from 0 to 4; and q is 1 or 2, or a pharmaceutically acceptable salt thereof.

[2] The pharmaceutical composition according to [1], wherein n is 0 or 1, p is 0, and q is 2.

[3] The pharmaceutical composition according to [1] or [2], wherein $R^4$ is a hydrogen atom, and $R^5$ is $COOR^6$.

[4] The pharmaceutical composition according to any one of [1] to [3], wherein $R^{1a}$ and $R^{1b}$ are independently selected from a hydrogen atom, a chlorine atom, a bromine atom, methyl and methoxy.

[5] The pharmaceutical composition according to any one of [1] to [4] comprising a compound represented by formula (Ia):

[Formula 2]

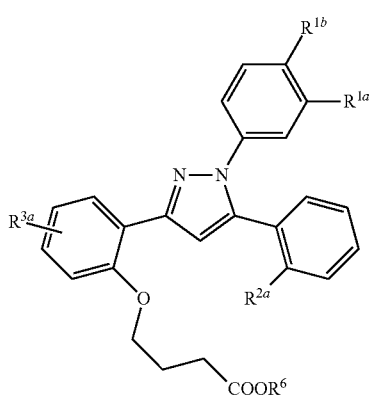

(Ia)

wherein, $R^{1a}$, $R^{1b}$, and $R^6$ as that defined in any one of [1] to [4], $R^{2a}$ is a hydrogen atom or a halogen atom, and $R^{3a}$ is a hydrogen atom or a halogen atom,
or a pharmaceutically acceptable salt thereof.

[6] The pharmaceutical composition according to any one of [1] to [5], wherein $R^6$ is a hydrogen atom.

[7] The composition according to [1] comprising a compound selected from the following, or a pharmaceutically acceptable salt thereof:
4-(2-(5-(2-chlorophenyl)-1-phenyl-1H-pyrazol-3-yl)phenoxy)butanoic acid;
4-(2-(1-(4-bromophenyl)-5-phenyl-1H-pyrazol-3-yl)phenoxy)butanoic acid;
4-(2-(1-(3,4-dichlorophenyl)-5-phenyl-1H-pyrazol-3-yl)phenoxy)butanoic acid;
4-(2-(1,5-diphenyl-1H-pyrazol-3-yl)phenoxy)butanoic acid;
4-(2-(1-(4-fluorophenyl)-5-phenyl-1H-pyrazol-3-yl)phenoxy)butanoic acid;
4-(2-(1-(4-chlorophenyl)-5-phenyl-1H-pyrazol-3-yl)phenoxy)butanoic acid;
4-(2-(5-phenyl-1-(4-isopropylphenyl)-1H-pyrazol-3-yl)phenoxy)butanoic acid;
4-(2-(1-(4-methoxyphenyl)-5-phenyl-1H-pyrazol-3-yl)phenoxy)butanoic acid;
4-(2-(1-(2-chlorophenyl)-5-phenyl-1H-pyrazol-3-yl)phenoxy)butanoic acid;
4-(2-(1-(3-chlorophenyl)-5-phenyl-1H-pyrazol-3-yl)phenoxy)butanoic acid;
4-(2-(5-(2-bromophenyl)-1-phenyl-1H-pyrazol-3-yl)phenoxy)butanoic acid; and
4-(2-(1,5-diphenyl-1H-pyrazol-3-yl)-4-fluorophenoxy)butanoic acid

[8] The pharmaceutical composition according to any one of [1] to [7], wherein synucleinopathy is Parkinson's disease, dementia with Lewy bodies, or multiple system atrophy.

[9] The pharmaceutical composition according to any one of [1] to [8] which is for use in oral administration.

[10] A compound represented by formula (Ib):

[Formula 3]

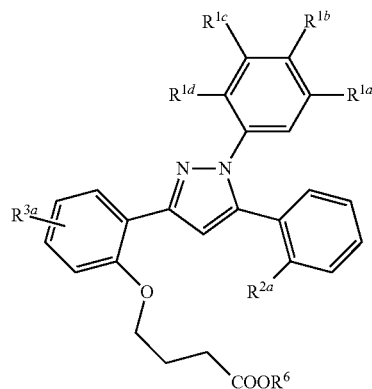

(Ib)

wherein $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;
$R^{2a}$ is a halogen atom;
$R^{3a}$ is a hydrogen atom or a halogen atom; and
$R^6$ is selected from a hydrogen atom, and $C_{1-6}$ alkyl,
or a pharmaceutically acceptable salt thereof.

[11] The compound according to [10] or a pharmaceutically acceptable salt thereof, wherein $R^{1d}$ is a hydrogen atom, or a halogen atom.

[12] The compound according to [10] or [11], or a pharmaceutically acceptable salt thereof, wherein $R^{2a}$ is a chlorine atom or a bromine atom.

[13] The compound according to [10] to [12], or a pharmaceutically acceptable salt thereof, wherein $R^{3a}$ is a hydrogen atom or a fluorine atom.

[14] A compound represented by formula (Ic):

[Formula 4]

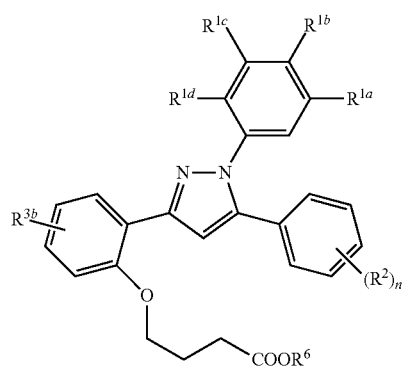

(Ic)

wherein, $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;
$R^2$ is $C_{1-6}$ alkyl, or a halogen atom;
n is an integer selected from 0 to 5;
$R^{3b}$ is a halogen atom;
$R^6$ is selected from a hydrogen atom, and $C_{1-6}$ alkyl,
or a pharmaceutically acceptable salt thereof.

[15] The compound according to [14] or a pharmaceutically acceptable salt thereof, wherein $R^{1d}$ is a hydrogen atom, or a halogen atom.

[16] The compound according to [14] or [15] or a pharmaceutically acceptable salt thereof, wherein n is 0 or 1.

[17] The compound according to any one of [14] to [16] or a pharmaceutically acceptable salt thereof, wherein $R^{3b}$ is a fluorine atom.

[18] A pharmaceutical composition for treating or preventing synucleinopathy comprising the compound according to any one of [10] to [17], or a pharmaceutically acceptable salt thereof.

[19] The pharmaceutical composition according to [18], wherein synucleinopathy is Parkinson's disease, dementia with Lewy bodies, or multiple system atrophy.

[20] The pharmaceutical composition according to [18] or [19] that is for use in oral administration.

The disclosure in the present specification further encompasses inventions disclosed in [1-1] to [1-22] below.

[1-1] A pharmaceutical composition for treating or preventing synucleinopathy comprising a compound represented by formula (I):

[Formula 5]

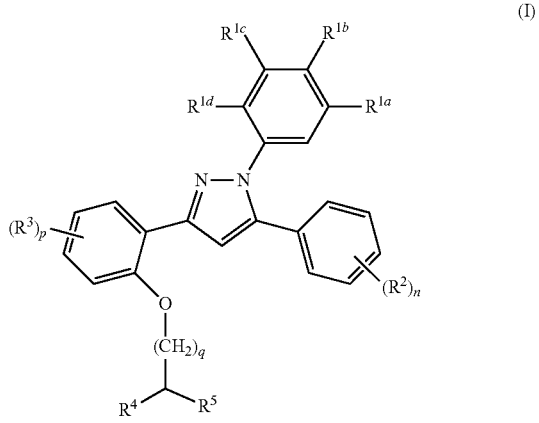

(I)

wherein, $R^{1a}$, $R^{1b}$ and $R^{1c}$ are independently selected from a hydrogen atom, $C_{1-6}$ alkyl, $C_{1-6}$ alkoxy, and a halogen atom;
$R^{1d}$ is a hydrogen atom, or a halogen atom;
$R^2$ and $R^3$ are independently selected from $C_{1-6}$ alkyl, and a halogen atom;
$R^4$ is selected from a hydrogen atom, and $C_{1-6}$ alkyl;
$R^5$ is selected from $COOR^6$, $CH_2OH$, and 1-tetrazolyl;
$R^6$ is selected from a hydrogen atom, and $C_{1-6}$ alkyl;
n is an integer selected from 0 to 5;
p is an integer selected from 0 to 4; and
q is 1 or 2,
or a pharmaceutically acceptable salt thereof.

[1-2] The pharmaceutical composition according to [1-1], wherein n is 0 or 1, p is 0 or 1, and q is 2.

[1-3] The pharmaceutical composition according to [1-1] or [1-2], wherein n is 0 or 1, p is 0, and q is 2.

[1-4] The pharmaceutical composition according to any one of [1-1] to [1-3], wherein $R^4$ is a hydrogen atom, and $R^5$ is $COOR^6$.

[1-5] The pharmaceutical composition according to any one of [1-1] to [1-4], wherein $R^{1a}$ and $R^{1b}$ are independently selected from a hydrogen atom, a chlorine atom, a bromine atom, methyl and methoxy.

[1-6] The pharmaceutical composition according to any one of [1-1] to [1-5] comprising a compound represented by formula (Ia):

[Formula 6]

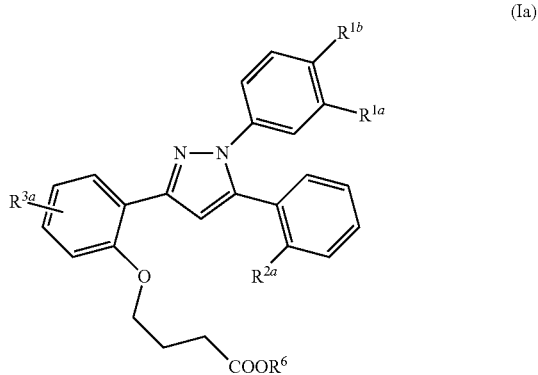

(Ia)

wherein, $R^{1a}$, $R^{1b}$, and $R^6$ are as defined in any one of [1-1] to [1-4], $R^{2a}$ is a hydrogen atom or a halogen atom, $R^{3a}$ is a hydrogen atom or a halogen atom, or a pharmaceutically acceptable salt thereof.

[1-7] The pharmaceutical composition according to any one of [1-1] to [1-6], wherein $R^{2a}$ is $C_{1-3}$ alkyl or a halogen atom.

[1-8] The pharmaceutical composition according to any one of [1-1] to [1-7], wherein $R^6$ is a hydrogen atom.

[1-9] The composition according to [1-1] comprising a compound selected from the following, or a pharmaceutically acceptable salt thereof:
4-(2-(5-(2-chlorophenyl)-1-phenyl-1H-pyrazol-3-yl)phenoxy)butanoic acid;
4-(2-(1-(4-bromophenyl)-5-phenyl-1H-pyrazol-3-yl)phenoxy)butanoic acid;
4-(2-(1-(3,4-dichlorophenyl)-5-phenyl-1H-pyrazol-3-yl)phenoxy)butanoic acid;
4-(2-(1,5-diphenyl-1H-pyrazol-3-yl)phenoxy)butanoic acid;
4-(2-(1-(4-fluorophenyl)-5-phenyl-1H-pyrazol-3-yl)phenoxy)butanoic acid;
4-(2-(1-(4-chlorophenyl)-5-phenyl-1H-pyrazol-3-yl)phenoxy)butanoic acid;
4-(2-(5-phenyl-1-(4-isopropylphenyl)-1H-pyrazol-3-yl)phenoxy)butanoic acid;
4-(2-(1-(4-methoxyphenyl)-5-phenyl-1H-pyrazol-3-yl)phenoxy)butanoic acid;
4-(2-(1-(2-chlorophenyl)-5-phenyl-1H-pyrazol-3-yl)phenoxy)butanoic acid;
4-(2-(1-(3-chlorophenyl)-5-phenyl-1H-pyrazol-3-yl)phenoxy)butanoic acid;
4-(2-(5-(2-bromophenyl)-1-phenyl-1H-pyrazol-3-yl)phenoxy)butanoic acid;
4-(2-(1,5-diphenyl-1H-pyrazol-3-yl)-4-fluorophenoxy)butanoic acid;
4-(2-(5-(2-chlorophenyl-1-phenyl-1H-pyrazol-3-yl)-4-fluorophenoxy)butanoic acid;
4-(2-(5-(2-chlorophenyl)-1-(4-isopropylphenyl)-1H-pyrazol-3-yl)-4-fluorophenoxy)butanoic acid;
4-(2-(5-(2-methylphenyl)-1-phenyl-1H-pyrazol-3-yl)-phenoxy)butanoic acid;
4-(2-(5-(2-bromophenyl)-1-(4-isopropylphenyl)-1H-pyrazol-3-yl)-4-fluorophenoxy)butanoic acid;

(S)-4-(2-(5-(2-chlorophenyl)-1-phenyl-1H-pyrazol-3-yl)-phenoxy)-2-methylbutanoic acid; and
(R)-4-(2-(5-(2-chlorophenyl)-1-phenyl-1H-pyrazol-3-yl)-phenoxy)-2-methylbutanoic acid.

[1-10] The pharmaceutical composition according to any one of [1-1] to [1-9], wherein synucleinopathy is Parkinson's disease, dementia with Lewy bodies, or multiple system atrophy.

[1-11] The pharmaceutical composition according to any one of [1-1] to [1-10] which is for use in oral administration.

[1-12] A compound represented by formula (Ib):

[Formula 7]

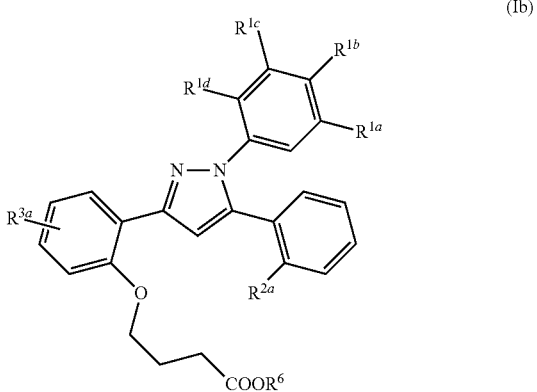

wherein $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;
$R^{2a}$ is selected from $C_{1-6}$ alkyl, and a halogen atom;
$R^{3a}$ is a hydrogen atom or a halogen atom; and
$R^6$ is selected from a hydrogen atom, and $C_{1-6}$ alkyl,
or a pharmaceutically acceptable salt thereof.

[1-13] The compound according to [1-12] or a pharmaceutically acceptable salt thereof, wherein $R^{1d}$ is a hydrogen atom, or a halogen atom.

[1-14] The compound according to [1-12] or [1-13], or a pharmaceutically acceptable salt thereof, wherein $R^{2a}$ is a chlorine atom or a bromine atom.

[1-15] The compound according to any one of [1-12] to [1-14], or a pharmaceutically acceptable salt thereof, wherein $R^{3a}$ is a hydrogen atom or a fluorine atom.

[1-16] A compound represented by formula (Ic):

[Formula 8]

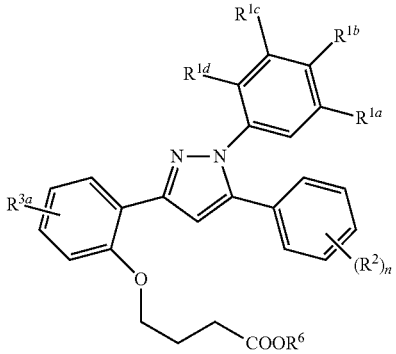

wherein, $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;
$R^2$ is $C_{1-6}$ alkyl, or a halogen atom;
n is an integer selected from 0 to 5;
$R^{3b}$ is a halogen atom;
$R^6$ is selected from a hydrogen atom, and $C_{1-6}$ alkyl,
or a pharmaceutically acceptable salt thereof.

[1-17] The compound according to [1-16] or a pharmaceutically acceptable salt thereof, wherein $R^{1d}$ is a hydrogen atom, or a halogen atom.

[1-18] The compound according to [1-16] or [1-17] or a pharmaceutically acceptable salt thereof, wherein n is 0 or 1.

[1-19] The compound according to any one of [1-16] to [1-18] or a pharmaceutically acceptable salt thereof, wherein $R^{3b}$ is a fluorine atom.

[1-20] A pharmaceutical composition for treating or preventing synucleinopathy comprising the compound according to any one of [1-12] to [1-19], or a pharmaceutically acceptable salt thereof.

[1-21] The pharmaceutical composition according to [1-20], wherein synucleinopathy is Parkinson's disease, dementia with Lewy bodies, or multiple system atrophy.

[1-22] The pharmaceutical composition according to [1-20] or [1-21] that is for use in oral administration.

The disclosure in the present specification further encompasses an invention disclosed in [2-1] to [2-17] below.

[2-1] A method for treating or preventing synucleinopathy comprising administering to a subject, an effective amount of a compound represented by formula (I):

[Formula 9]

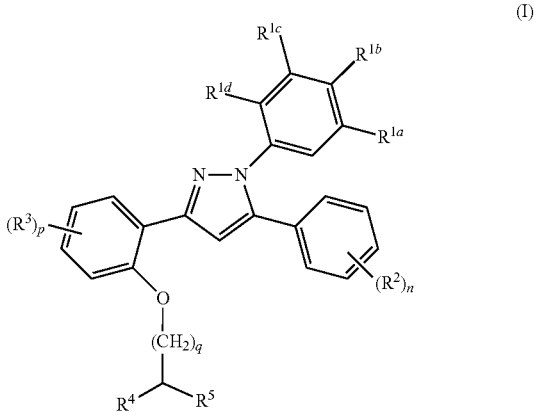

wherein, $R^{1a}$, $R^{1b}$ and $R^{1c}$ are independently selected from a hydrogen atom, $C_{1-6}$ alkyl, $C_{1-6}$ alkoxy, and a halogen atom;
$R^{1d}$ is a hydrogen atom, or a halogen atom;
$R^2$ and $R^3$ are independently selected from $C_{1-6}$ alkyl, and a halogen atom;
$R^4$ is selected from a hydrogen atom, and $C_{1-6}$ alkyl;
$R^5$ is selected from $COOR^6$, $CH_2OH$, and 1-tetrazolyl;
$R^6$ is selected from a hydrogen atom, and $C_{1-6}$ alkyl;
n is an integer selected from 0 to 5;
p is an integer selected from 0 to 4; and
q is 1 or 2,
or a pharmaceutically acceptable salt thereof.

[2-2] The method according to [2-1], wherein n is 0 or 1, p is 0, and q is 2.

[2-3] The method according to [2-1] or [2-2], wherein $R^4$ is a hydrogen atom, and $R^5$ is $COOR^6$.

[2-4] The method according to any one of [2-1] to [2-3], wherein $R^{1a}$ and $R^{1b}$ are independently selected from a hydrogen atom, a chlorine atom, a bromine atom, methyl and methoxy.

[2-5] The method according to any one of [2-1] to [2-4] comprising a compound represented by formula (Ia):

[Formula 10]

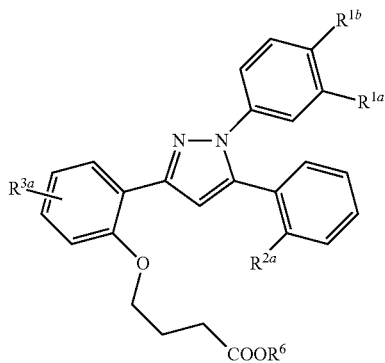

wherein, $R^{1a}$, $R^{1b}$, and $R^6$ are as defined in any one of [2-1] to [2-4], $R^{2a}$ is a hydrogen atom or a halogen atom, $R^{3a}$ is a hydrogen atom or a halogen atom, or a pharmaceutically acceptable salt thereof.

[2-6] The method according to any one of [2-1] to [2-5], wherein $R^4$ is a hydrogen atom.

[2-7] The method according to [2-1] wherein the compound or the pharmaceutically acceptable salt thereof is a compound selected from the following, or a pharmaceutically acceptable salt thereof:

4-(2-(5-(2-chlorophenyl)-1-phenyl-1H-pyrazol-3-yl)phenoxy)butanoic acid;
4-(2-(1-(4-bromophenyl)-5-phenyl-1H-pyrazol-3-yl)phenoxy)butanoic acid;
4-(2-(1-(3,4-dichlorophenyl)-5-phenyl-1H-pyrazol-3-yl)phenoxy)butanoic acid;
4-(2-(1,5-diphenyl-1H-pyrazol-3-yl)phenoxy)butanoic acid;
4-(2-(1-(4-fluorophenyl)-5-phenyl-1H-pyrazol-3-yl)phenoxy)butanoic acid;
4-(2-(1-(4-chlorophenyl)-5-phenyl-1H-pyrazol-3-yl)phenoxy)butanoic acid;
4-(2-(5-phenyl-1-(4-isopropylphenyl)-1H-pyrazol-3-yl)phenoxy)butanoic acid;
4-(2-(1-(4-methoxyphenyl)-5-phenyl-1H-pyrazol-3-yl)phenoxy)butanoic acid;
4-(2-(1-(2-chlorophenyl)-5-phenyl-1H-pyrazol-3-yl)phenoxy)butanoic acid;
4-(2-(1-(3-chlorophenyl)-5-phenyl-1H-pyrazol-3-yl)phenoxy)butanoic acid;
4-(2-(5-(2-bromophenyl)-1-phenyl-1H-pyrazol-3-yl)phenoxy)butanoic acid;
4-(2-(1,5-diphenyl-1H-pyrazol-3-yl)-4-fluorophenoxy)butanoic acid;
4-(2-(5-(2-chlorophenyl-1-phenyl-1H-pyrazol-3-yl)-4-fluorophenoxy)butanoic acid;
4-(2-(5-(2-chlorophenyl)-1-(4-isopropylphenyl)-1H-pyrazol-3-yl)-4-fluorophenoxy)butanoic acid;
4-(2-(5-(2-methylphenyl)-1-phenyl-1H-pyrazol-3-yl)-phenoxy)butanoic acid;
4-(2-(5-(2-bromophenyl)-1-(4-isopropylphenyl)-1H-pyrazol-3-yl)-4-fluorophenoxy)butanoic acid;
(S)-4-(2-(5-(2-chlorophenyl)-1-phenyl-1H-pyrazol-3-yl)-phenoxy)-2-methylbutanoic acid; and
(R)-4-(2-(5-(2-chlorophenyl)-1-phenyl-1H-pyrazol-3-yl)-phenoxy)-2-methylbutanoic acid.

[2-8] The method according to any one of [2-1] to [2-7], wherein synucleinopathy is Parkinson's disease, dementia with Lewy bodies, or multiple system atrophy.

[2-9] The method according to any one of [2-1] to [2-8], wherein the compound or a pharmaceutically acceptable salt thereof is orally administered.

[2-10] A method according to [2-1], wherein the compound or the pharmaceutically acceptable salt thereof is a compound represented by formula (Ib):

[Formula 11]

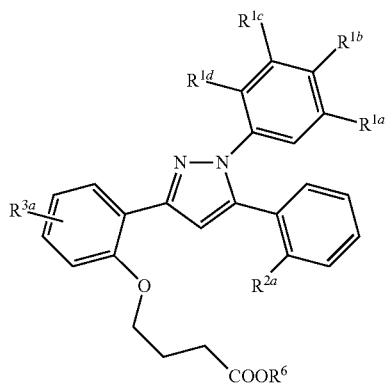

wherein $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;
$R^{2a}$ is a halogen atom;
$R^{3a}$ is a hydrogen atom or a halogen atom; and
$R^6$ is selected from a hydrogen atom, and $C_{1-6}$ alkyl,
or a pharmaceutically acceptable salt thereof.

[2-11] The method according to [2-10], wherein $R^{1d}$ is a hydrogen atom, or a halogen atom.

[2-12] The method according to [2-10] or [2-11], wherein $R^{2a}$ is a chlorine atom or a bromine atom.

[2-13] The method according to any one of [2-10] to [2-12], wherein $R^{3a}$ is a hydrogen atom or a fluorine atom.

[2-14] A method according to [2-1], wherein the compound or the pharmaceutically acceptable salt thereof is a compound represented by formula (Ic):

[Formula 12]

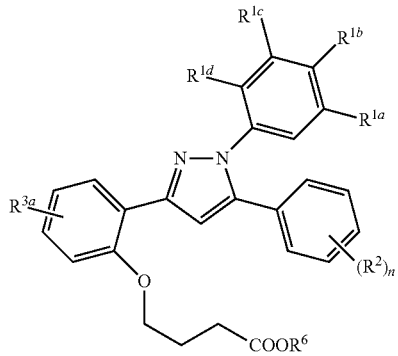

wherein, $R^{1a}$, $R^{1b}$, Rio and $R^{1d}$ are independently selected from a hydrogen atom, $C_{1-6}$ alkyl, $C_{1-6}$ alkoxy, and a halogen atom;

$R^2$ is $C_{1-6}$ alkyl, or a halogen atom;
n is an integer selected from 0 to 5;
$R^{3b}$ is a halogen atom;
$R^6$ is selected from a hydrogen atom, and $C_{1-6}$ alkyl,
or a pharmaceutically acceptable salt thereof.

[2-15] The method according to [2-14], wherein $R^{1d}$ is a hydrogen atom, or a halogen atom.

[2-16] The method according to [2-14] or [2-15], wherein n is 0 or 1.

[2-17] The method according to any one of [2-14] to [2-16], wherein $R^{3b}$ is a fluorine atom.

Advantageous Effects of Invention

In one aspect, the present invention provides a pharmaceutical composition to use for treating or preventing synucleinopathy. In another aspect, the present invention provides a compound having a therapeutic or prophylactic effect against synucleinopathy.

BRIEF DESCRIPTION OF DRAWING

FIG. 14 is a diagram showing the procedures of the rotarod test, the beam walking test, and the novel object recognition test conducted in the Test Examples.

FIG. 15 is a diagram showing the base sequence subjected to sequencing in Test Example 13.

DESCRIPTION OF EMBODIMENTS

Figure 1:
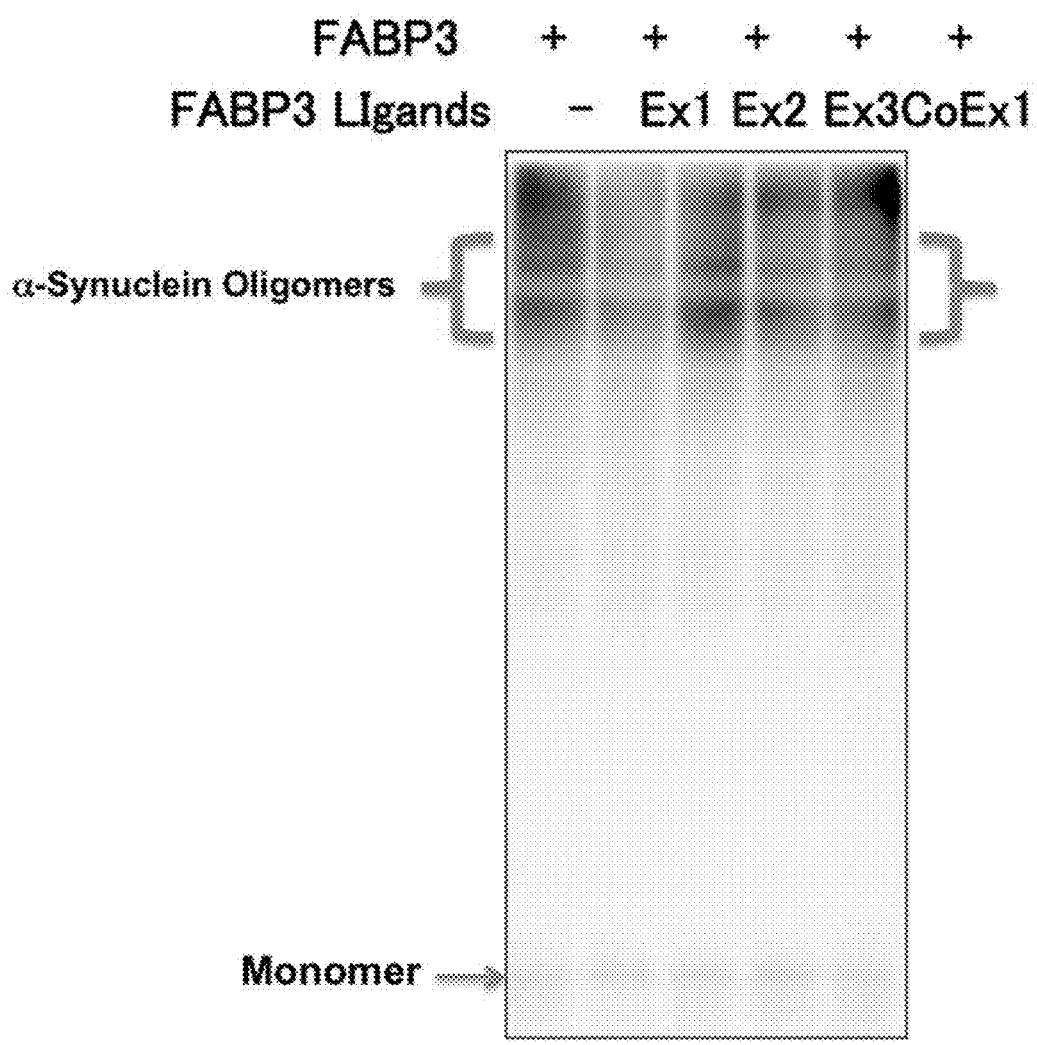
FIG. 1 is Western blotting showing the result of an oligomer forming inhibition test of α-synuclein using PC12 cells that were transfected with genes expressing α-synuclein and FABP3. It was confirmed that, whereas the compounds of Examples 1 to 3 (Ex1 to Ex3), which are FABP3 ligands, showed an oligomer forming inhibition effect, the compound of Comparative Example 1 (CoEx1) did not show such effect.

The present invention is described in more detail below.
According to one aspect of the present invention, a pharmaceutical composition is provided for treating or preventing a disease or disorder of the cognitive function, comprising a compound represented by formula (I) or a pharmaceutically acceptable salt thereof as an active component. In one embodiment, a pharmaceutical composition is provided for treating or preventing a disease or disorder of the cognitive function, comprising a compound represented by formula (Ia) or formula (Ib) as an active component. In the present specification, the compound represented by formula (I) encompasses a compound represented by formula (Ia) or formula (Ib).

As used in this specification, "$C_{1-6}$ alkyl" refers to a straight chain, branched chain, cyclic or partially cyclic alkyl group with 1 to 6 carbons, which includes, for example, methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl, cyclopropyl, cyclobutyl, cyclopentyl, cyclohexyl, and cyclopropylmethyl, and also includes $C_{1-4}$ alkyl and $C_{1-3}$ alkyl.

As used in this specification, "$C_{1-6}$ alkoxy" refers to an alkyloxy group [—O—($C_{1-6}$ alkyl)] comprising an alkyl group having 1 to 6 carbons, defined previously, as the alkyl section, which includes, for example, methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, cyclopentyloxy, cyclohexyloxy, cyclopropylmethyloxy, and also includes $C_{1-4}$ alkoxy and $C_{1-3}$ alkoxy.

The functional group indicated by 1-tetrazolyl is as follows.

[Formula 13]

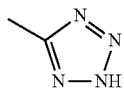

Examples of halogen atoms include a fluorine atom, a chlorine atom, a bromine atom, and an iodine atom.

If n is 0 in formula (I), the substituent represented by $R^2$ does not exist. If p is 0, the substituent represented by $R^3$ does not exist.

In one embodiment of the invention, $R^{1a}$, $R^{1b}$, $R^{1c}$ and $R^{1d}$ in formula (Ib) and formula (Ic) are independently selected from a hydrogen atom, $C_{1-6}$ alkyl, $C_{1-6}$ alkoxy, and a halogen atom.

When the compound of formula (I) or the pharmaceutically acceptable salt thereof forms a solvate, such as a hydrate, the present invention may be performed using said solvate. Further, the compound of the present invention or a pharmaceutically acceptable salt thereof may be implemented appropriately as a mixture, a solution or a crystal polymorphism.

By way of example, compounds shown in the Examples in this specification may be used as compounds of the present invention, and more specifically, the following compounds may be used.

The "pharmaceutically acceptable salt" of the compound of formula (I) is not particularly limited as long as it can be used as a pharmaceutical product. Salts that the compound of the present invention forms with a base include salts with inorganic bases such as sodium, potassium, magnesium, calcium, aluminum; and salts with organic bases such as methylamine, ethylamine and ethanolamine. The salt may also be an acid addition salt, and such salts specifically include acid addition salts with mineral acids such as hydrochloric acid, hydrobromic acid, hydroiodic acid, sulfuric acid, nitric acid, and phosphate; and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid. Given as a preferable example of a pharmaceutically acceptable salt is the base addition salt of a compound of formula (I) that is a carboxylic acid.

According to one embodiment of the present invention, the compound of formula (I), an enantiomer thereof, a diastereomer thereof, or a pharmaceutically acceptable salt thereof is administered as a prodrug, and is transformed into an active compound in vivo.

Examples of compounds included in formula (I) include the compound in the Examples and the following compounds.

[Formula 14]

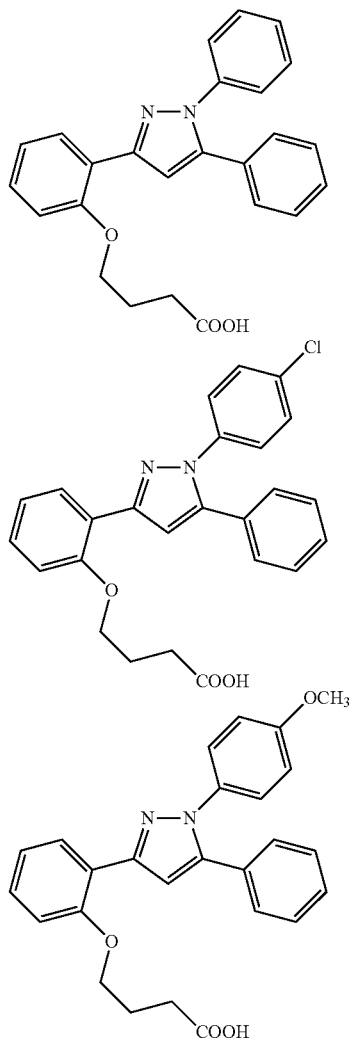

Synucleinopathies as used herein refer to neurodegenerative diseases characterized by the abnormal accumulation of α-synuclein, exemplified by Parkinson's disease, dementia with Lewy bodies, or multiple system atrophy, and the pharmaceutical composition and method of the present invention may be used to suppress the progress of synucleinopathy.

In the pharmaceutical composition and method of the present invention, there is no particular limitation to the degree of progression, severity and pathosis of synucleinopathy to be treated. As classification of the severity of Parkinson's disease is used the Yahr scale of I to V. The stages of dementia with Lewy bodies are divided into the early stage, the middle stage, and the late stage, and the disease is separated into brain stem dominant, limbic and neocortical types based on the area where the α-synuclein inclusion appears first. Further, in the severity classification of multiple system atrophy, the modified Ranking Scale 1 to 6 is used, and the disease is classified by pathosis into Shy Drager syndrome, olivopontocerebellar atrophy, and striatonigral degeneration. All of these are disease groups in which the α-synuclein inclusion is expressed in the neuron cell or the glial cell, and the pharmaceutical composition and method of the present invention may be used for treating or preventing the disease selected from these disease groups.

It is believed that a cognitive disorder develops by the nerve cell death of the frontal cortex or the hippocampus. The present invention proposes that the FABP3 ligand suppresses aggregation and also suppresses propagation of the α-synuclein aggregate. As a result, the nerve cell death by the α-synuclein aggregate in the brain is suppressed.

The pharmaceutical composition and method of the present invention can be used particularly for treating and preventing dementia with Lewy bodies.

Further, the pharmaceutical composition and method of the present invention can ameliorate motor dysfunction and cognitive dysfunction as well as suppress the progression thereof.

Examples of motor dysfunction seen in the Parkinson's disease are tremor (shaking of hand and feet), akinesia (slow movement), rigidity (the muscle becomes rigid and stiffens, and resistance is felt in the bending and stretching of the joint), and postular reflex disorder (difficulty experienced in balancing the body); seen in the dementia with Lewy bodies is parkinsonism; and seen in multiple system atrophy are not just parkinsonism, but also autonomic disorder (dysuria, erectile disorder, orthostatic hypotension, hypohidrosis, etc.), cerebellar ataxia (ataxic gait and dysarthria, ataxia of extremities, or cerebellar oculomotor dysfunction).

Examples of cognitive dysfunction seen in dementia with Lewy bodies are memory disorder, frontal lobe/parietal lobe dysfunction (attention disorder, visual space disorder, constructional disorder, executional functional disorder), fluctuation in the cognitive function, and visual hallucination. Seen in the Parkinson's disease at an early stage are higher brain dysfunctions such as that in the executional function (planning, transformation/retention of a set, problem solving, etc.), memory function such as working memory, procedural memory, and visual spatial function, and when the disease progresses, symptoms similar to dementia with Lewy bodies develop, such as visual hallucination, visual space cognitive disorder, and slow thought. Seen in multiple system atrophy is a cognitive disorder such as short memory.

The pharmaceutical composition of the present invention may be in various dosage forms, including the following, without being limited thereby: for oral administration, tablets, capsules, dispersants, granules, pills, liquid drugs, emulsions, suspensions, solutions, spirits, syrups, extracts, elixirs; and for non-oral drugs, injectables such as hypodermic agents, intravenous injection agent, intramuscular injection agent, and intraperitoneal injection agent, endermism or patches, ointments or lotions; for intraoral administration, sublingual agent, oral cavity patch; and for nasal administration, aerosol agent. These formulations may be manufactured by a publicly known method that is commonly used in the formulation step.

The pharmaceutical composition may include various components that are commonly applied, which may include one or more of an excipient, disintegrator, diluent, lubricant, flavoring agent, coloring agent, sweetener, corrective agent, suspending agent, wetting agent, emulsifier, dispersant, adjuvant, antiseptic, buffer, binding agent, stabilizer, and coating agent, which is pharmaceutically acceptable. Also, the pharmaceutical composition of the present invention may be in a prolonged or sustained-release form.

The dosage of the pharmaceutical composition of the present invention may be appropriately selected by the administration route, the body shape, age, physical condition of the patient, the level of the disease, and the time from onset, and the pharmaceutical composition of the present invention may include a compound of formula (I) in a therapeutically effective and/or prophylactically effective amount. The compound of formula (I) in the present invention may be used at a dosage of 1 to 1000 mg/day/adult, for example 1 to 200 mg/day/adult, specifically 5 to 100 mg/day/adult, more specifically 10 to 50 mg/day/adult. The pharmaceutical composition may be administered at once or over multiple times.

The pharmaceutical composition of the present invention may include components such as the conventionally known coloring agent, preservative, flavoring agent, savor agent, coating agent, antioxidant, vitamin, amino acid, peptide, protein and minerals (iron, zinc, magnesium, iodo, etc.). The pharmaceutical composition of the present invention may be in a form suitable for oral administration, including forms of various solid formulations, such as granules (including dry syrup), capsules (soft capsules, hard capsules), tablets (chewable agents), dispersants (powder agents), pills, or forms of liquid formulation such as orally administered liquid agents (liquid agent, suspension, syrups).

Additives added during formulation include an excipient, lubricant, binding agent, disintegrator, fluidization agent, dispersant, wetting agent, antiseptic, viscous agent, pH adjustor, coloring agent, corrective agent, surfactant, and dissolution adjuvant. When formulating a liquid agent, thickeners such as pectin, xanthan gum, or guar gum may be added. A coating agent may be used to obtain a coating tablet or a paste-like glue agent. The agents may be formulated into other dosage forms by following the conventional method.

The therapeutic method or prophylactic method of the present invention may be implemented according to the above description. An example of a subject to which the compound of formula (I) or a pharmaceutically acceptable salt thereof is administered is a mammal, such as a human.

EXAMPLES

The present invention is described in more detail below by using Examples, but without being limited by these Examples.

Example 1: 4-(2-(5-(2-Chlorophenyl)-1-phenyl-1H-pyrazol-3-yl)phenoxy)butanoic acid

[Step 1] Preparation of (E)-3-(2-chlorophenyl)-1-(2-methoxyphenyl)prop-2-en-1-one

[Formula 15]

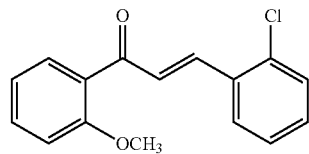

2'-Methoxyacetophenone (1.0 g, 6.7 mmol, 1.0 eq) and 2.5 mol/L sodium hydroxide aqueous solution (30 ml) were dissolved in ethanol (50 ml), and the solution was stirred at 0° C. for 30 min. before adding 2-chlorobenzaldehyde (1.123 g, 8.0 mmol, 1.2 eq) dropwise, then the mixture was stirred for two days at room temperature. Ethanol was removed by evaporation, the remaining mixture was extracted with ethyl acetate, and the organic phase was dried with anhydrous magnesium sulfate and concentrated to obtain the subject compound as a solid (2.178 g, yield 100%).

Rf value: 0.21 (n-hexane/ethyl acetate=7:1 v/v).

$^1$H-NMR (300 MHz, CDCl$_3$) δ: 8.01 (d, J=16.0 Hz, 1H), 7.71-7.62 (m, 2H), 7.50-7.39 (m, 2H), 7.35 (d, J=16.0 Hz, 1H), 7.30-7.26 (m, 2H), 7.06-6.98 (m, 2H), 3.89 (s, 3H).

[Step 2] Preparation of 5-(2-chlorophenyl)-3-(2-methoxyphenyl)-1-phenyl-1H-pyrazole

[Formula 16]

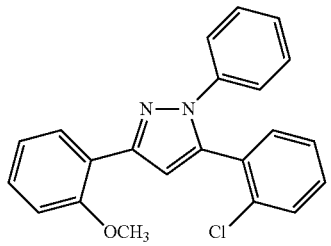

(E)-3-(2-Chlorophenyl)-1-(2-methoxyphenyl)prop-2-en-1-one (2.02 g, 7.4 mmol, 1.0 eq) and phenylhydrazine (1.1 ml, 11.2 mmol, 1.5 eq) were dissolved in ethanol (50 ml), to which acetic acid (2 ml) was added, and the mixture was stirred overnight with heating to reflux under an argon atmosphere. The mixture was extracted with ethyl acetate, and the organic phase was washed with water, dried with anhydrous magnesium sulfate and concentrated. The obtained crude intermediate product was dissolved in benzene (30 ml), to which DDQ (2.52 g, 11.1 mmol, 1.5 eq) was added, and the mixture was stirred overnight with heating to reflux. The reaction mixture was brought to room temperature and filtered through Celite using ethyl acetate. The filtrate was concentrated, and the residue was purified using silica gel column chromatography (silica gel 60, eluant: n-hexane/ethyl acetate=8:1 v/v) to obtain the subject compound (2.387 g, yield: 89.3%).

Rf value: 0.31 (n-hexane/ethyl acetate=8:1 v/v).

$^1$H-NMR (300 MHz, CDCl$_3$) δ: 8.16 (dd, J=7.6, 1.8 Hz, 1H), 7.42-7.40 (m, 1H), 7.36-7.21 (m, 9H), 7.11 (s, 1H), 7.05 (td, J=7.5, 1.2 Hz, 1H), 7.00 (dd, J=8.3, 0.9 Hz, 1H), 3.93 (s, 3H).

[Step 3] Preparation of 5-(2-chlorophenyl)-3-(2-hydroxyphenyl)-1-phenyl-1H-pyrazole

[Formula 17]

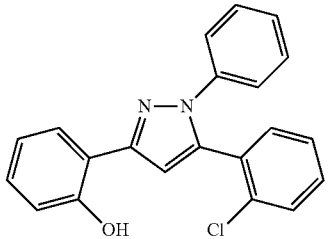

5-(2-Chlorophenyl)-3-(2-methoxyphenyl)-1-phenyl-1H-pyrazole (1.71 g, 4.7 mmol, 1.0 eq) was dissolved in anhydrous dichloromethane (30 ml), and boron tribromide (17% dichloromethane solution, about 1 mol/L) (9.45 ml, 9.45 mmol, 2.0 eq) was added dropwise at −10° C. under an argon atmosphere, then the mixture was stirred overnight while being brought to room temperature. The reaction was quenched with saturated sodium hydrogen carbonate aqueous solution, the reaction mixture was extracted with dichloromethane, and the organic phase was dried with anhydrous magnesium sulfate and concentrated. The residue was purified using silica gel column chromatography (silica gel 60, eluant: n-hexane/ethyl acetate=9:1 v/v) to obtain the subject compound (1.41 g, yield: 86.2%).

Rf value: 0.32 (n-hexane/ethyl acetate=9:1 v/v).

$^1$H-NMR (400 MHz, CDCl$_3$) δ: 10.82 (s, 1H), 7.64 (dd, J=7.7, 1.7 Hz, 1H), 7.43 (dq, J=8.0, 0.6 Hz, 1H), 7.38-7.24 (m, 9H), 7.07 (dd, J=8.2, 1.2 Hz, 1H), 6.97-6.93 (m, 1H), 6.90 (s, 1H).

[Step 4] Preparation of ethyl 4-(2-(5-(2-chlorophenyl)-1-phenyl-1H-pyrazol-3-yl)phenoxy)butyrate

[Formula 18]

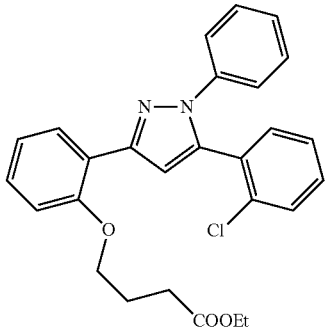

A solution of 5-(2-chlorophenyl)-3-(2-hydroxyphenyl)-1-phenyl-1H-pyrazole (1.14 g, 3.3 mmol, 1.0 eq), ethyl 4-bromobutyrate (0.64 g, 3.3 mmol, 1.0 eq), potassium carbonate (0.45 g, 3.3 mmol, 1.0 eq), and potassium iodide (0.54 g, 3.3 mmol, 1.0 eq) in dry DMF (50 ml) was stirred at 70° C. After 24 hours, ethyl 4-bromobutyrate (0.64 g, 3.3 mmol, 1.0 eq), potassium carbonate (0.45 g, 3.3 mmol, 1.0 eq) and potassium iodide (0.54 g, 3.3 mmol, 1.0 eq) were further added, and the mixture was stirred at 70° C. for one more night. The reaction mixture was brought back to room temperature, 1 mol/L hydrochloric acid was added to the mixture and then the mixture was extracted with ethyl acetate. The organic phase was washed with a saturated sodium hydrogen carbonate aqueous solution and saturated brine, then dried with anhydrous magnesium sulfate and concentrated. The residue was purified using silica gel column chromatography (n-hexane/ethyl acetate=8:1 v/v, Rf=0.16) to obtain the subject compound (1.602 g, yield: 100%) which was slightly yellow and oil-like.

Rf value: 0.16 (n-hexane/ethyl acetate=8:1 v/v).

$^1$H-NMR (300 MHz, CDCl$_3$) δ: 8.14 (dd, J=7.7, 1.7 Hz, 1H), 7.44-7.41 (m, 1H), 7.35-7.21 (m, 9H), 7.08 (s, 1H), 7.05 (td, J=7.5, 1.1 Hz, 1H), 6.98 (d, J=8.2 Hz, 1H), 4.16-4.07 (m, 4H), 2.57 (t, J=7.4 Hz, 2H), 2.24-2.15 (m, 2H), 1.22 (t, J=7.2 Hz, 3H).

[Step 5] Preparation of 4-(2-(5-(2-chlorophenyl)-1-phenyl-1H-pyrazol-3-yl)phenoxy)butanoic acid

[Formula 19]

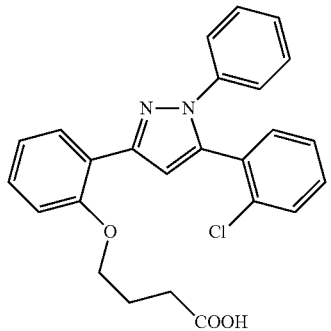

Ethyl 4-(2-(5-(2-chlorophenyl)-1-phenyl-1H-pyrazol-3-yl)phenoxy)butyrate (5.00 g, 10.8 mmol) was dissolved in a mixed solvent of 2.5 mol/L sodium hydroxide aqueous solution (50 mL) and ethanol (25 mL), and subjected to reflux overnight. Ethanol was removed by evaporation, the residue, after having dilute hydrochloric acid added to it, was extracted with ethyl acetate, and the organic phase was dried with anhydrous magnesium sulfate and concentrated. The residue was purified using a silica gel column chromatography (n-hexane/ethyl acetate=1:1 v/v, Rf 0.37), and the subject compound was obtained (3.54 g, yield: 74.3%).

Rf value: 0.37 (n-hexane/ethyl acetate=1:1 (v/v)), melting point: 85.5-86.5° C., chemical purity: 98% (area % of reverse phase HPLC, detection UV wavelength: 254 nm).

$^1$H-NMR: (300 MHz CDCl$_3$) δ: 8.00 (1H, dd, J=7.7, 1.7 Hz), 7.43-7.40 (1H, m), 7.35-7.21 (9H, m), 7.06 (1H, td, J=7.5, 1.1 Hz), 7.00 (1H, s), 6.99 (1H, d, J=7.3 Hz), 4.15 (2H, t, J=6.0 Hz), 2.60 (2H, t, J=7.2 Hz), 2.19 (2H, quin, J=6.7 Hz).

Mass spectrometry value (FAB (M+1)+): 433.2.

Example 2: 4-(2-(1-(4-Bromophenyl)-5-phenyl-1H-pyrazol-3-yl)phenoxy)butanoic acid

[Formula 20]

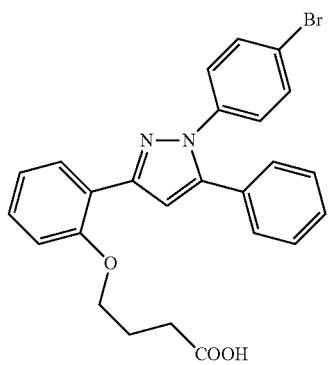

The subject compound was prepared in the same manner as Example 1, except for using benzaldehyde instead of 2-chlorobenzaldehyde in Step 1, and 4-bromophenylhydrazine instead of phenylhydrazine in Step 2.

$^1$H NMR (400 MHz, CDCl$_3$): δ: 7.97 (dd, J=7.6, 1.6 Hz, 1H), 7.46 (d, J=8.4 Hz, 2H), 7.35-7.23 (m, 8H), 7.05 (dd, J=7.6, 7.6 Hz, 1H), 6.99 (d, J=8.0 Hz, 1H), 6.99 (s, 1H), 4.15 (t. J=6.0 Hz, 2H), 2.62. (t, J=7.2 Hz, 2H), 2.24-2.17 (m, 2H).

High resolution mass spectrometry (FAB, [M+H]$^+$) $C_{25}H_{22}BrN_2O_3$ Calculated value 477.0814; Actual measurement 477.0812.

Example 3: 4-(2-(1-(3,4-Dichlorophenyl)-5-phenyl-1H-pyrazol-3-yl)phenoxy)butanoic acid

[Formula 21]

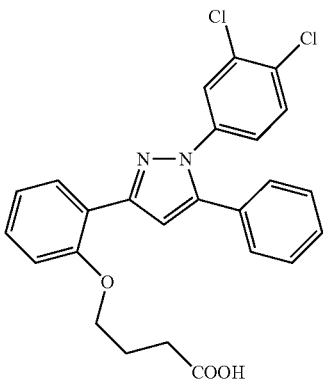

The subject compound was prepared in the same manner as Example 1, except for using benzaldehyde instead of 2-chlorobenzaldehyde in Step 1, and 3,4-dichlorophenylhydrazine instead of phenylhydrazine in Step 2.

$^1$H NMR (400 MHz, CDCl$_3$): δ=8.00 (dd, J=7.6, 1.6 Hz, 1H), 7.62 (d, J=2.8 Hz, 1H), 7.38-7.28 (m, 7H), 7.12-6.98 (m, 4H), 4.16 (t, J=6.4 Hz, 2H), 2.64 (t, J=7.2 Hz, 2H), 2.25-2.18 (m, 2H).

High resolution mass spectrometry (FAB, [M+H]$^+$) $C_{25}H_{21}Cl_2N_2O_3$, Calculated value 467.0929, Actual measurement 467.0942.

Example 4: 4-(2-(5-(2-Bromophenyl)-1-phenyl-1H-pyrazol-3-yl)phenoxy)butanoic acid

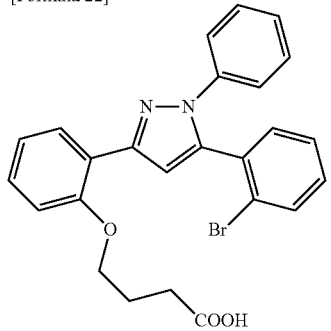

[Formula 22]

The subject compound was prepared in the same manner as Example 1, except for using 2-bromobenzaldehyde instead of 2-chlorobenzaldehyde in Step 1.

$^1$H NMR (400 MHz, CDCl$_3$): δ=8.03 (dd, J=7.6, 1.6 Hz, 1H), 7.61 (d, J=7.6 Hz, 1H), 7.34-7.20 (m, 9H), 7.05 (ddd, J=7.6, 7.6, 1.2 Hz, 1H), 7.00-6.98 (m, 2H), 4.15 (t, J=6.0 Hz, 2H), 2.61 (t, J=7.2 Hz, 2H), 2.22-2.16 (m, 2H).

High resolution mass spectrometry (FAB, [M+H]$^+$) C$_{25}$H$_{22}$BrN$_2$O$_3$ Calculated value 479.0793; Actual measurement 479.0800.

Example 5: 4-(2-(1-(4-isopropylphenyl)-5-phenyl-1H-pyrazol-3-yl)phenoxy)butanoic acid

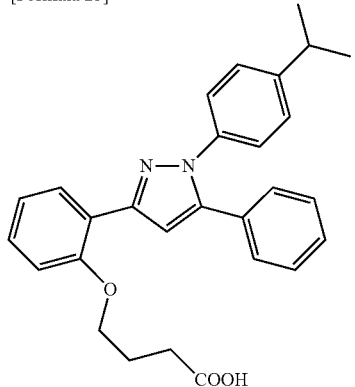

[Formula 23]

The subject compound was prepared in the same manner as Example 1, except for using benzaldehyde instead of 2-chlorobenzaldehyde in Step 1, and 4-isopropylphenylhydrazine instead of phenylhydrazine in Step 2.

$^1$H NMR (400 MHz, CDCl$_3$): δ=7.93 (dd, J=7.8, 1.8 Hz, 1H), 7.30-7.26 (m, 8H), 7.21-7.18 (m, 2H), 7.06-6.95 (m, 3H), 4.15 (t, J=6.0 Hz, 2H), 2.95-2.88 (m, 1H), 2.59 (t, J=7.2 Hz), 2.23-2.16 (m, 2H), 1.25-1.23 (m, 6H).

High resolution mass spectrometry (FAB, [M+H]$^+$) C$_{28}$H$_{29}$N$_2$O$_3$, Calculated value 441.2178, Actual measurement 441.2177.

Example 6: 4-(2-(1-(3-Chlorophenyl)-5-phenyl-1H-pyrazol-3-yl)phenoxy)butanoic acid

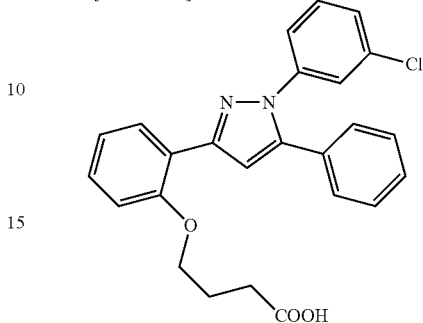

[Formula 24]

The subject compound was prepared in the same manner as Example 1, except for using benzaldehyde instead of 2-chlorobenzaldehyde in Step 1, and 3-chlorophenylhydrazine instead of phenylhydrazine in Step 2.

$^1$H NMR (400 MHz, CDCl$_3$): δ=8.01 (dd, J=7.8, 1.8 Hz, 1H), 7.51-7.50 (m, 1H), 7.35-7.21 (m, 8H), 7.18-7.15 (m, 1H), 7.07-7.03 (m, 1H), 7.01-6.98 (m, 2H), 4.16 (t, J=6.0 Hz, 2H), 2.64 (t, J=7.2 Hz), 2.25-2.18 (m, 2H).

High resolution mass spectrometry (FAB, [M+H]$^+$) C$_{25}$H$_{22}$ClN$_2$O$_3$, Calculated value 433.1319, Actual measurement 433.1330.

Example 7: 4-(2-(1-(4-Fluorophenyl)-5-phenyl-1H-pyrazol-3-yl)phenoxy)butanoic acid

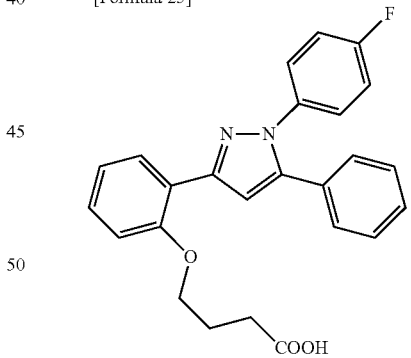

[Formula 25]

The subject compound was prepared in the same manner as Example 1, except for using benzaldehyde instead of 2-chlorobenzaldehyde in Step 1, and 4-fluorophenylhydrazine instead of phenylhydrazine in Step 2.

$^1$H NMR (400 MHz, CDCl$_3$): δ=7.96 (dd, J=7.6, 1.6 Hz, 1H), 7.36-7.26 (m, 8H), 7.07-7.02 (m, 3H), 6.99 (d, J=7.6 Hz, 1H), 6.98 (s, 1H), 4.16 (t, J=6.4 Hz, 2H), 2.62 (t, J=7.2 Hz, 2H), 2.24-2.18 (m, 2H).

High resolution mass spectrometry (FAB, [M+H]$^+$) C$_{25}$H$_{22}$FN$_2$O$_3$, Calculated value 417.1614, Actual measurement 417.1622.

Example 8: 4-(2-(1-(4-tert-Butylphenyl)-5-phenyl-1H-pyrazol-3-yl)phenoxy)butanoic acid

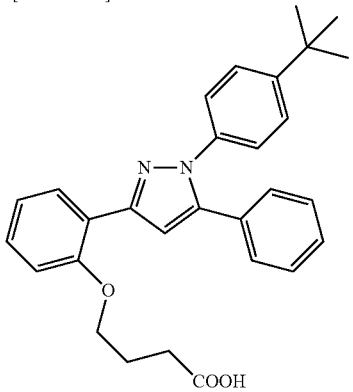

[Formula 26]

The subject compound was prepared in the same manner as Example 1, except for using benzaldehyde instead of 2-chlorobenzaldehyde in Step 1, and 4-tert-butylphenylhydrazine instead of phenylhydrazine in Step 2.

$^1$H NMR (400 MHz, CDCl$_3$): δ=7.96 (dd, J=7.6, 2.0 Hz, 1H), 7.37-7.27 (m, 10H), 7.06-7.02 (m, 1H), 6.99 (d, J=8.0 Hz, 1H), 6.96 (s, 1H), 4.15 (t, J=6.0 Hz, 2H), 2.60 (t, J=7.6 Hz, 2H), 2.23-2.17 (m, 2H), 1.31 (s, 9H).

High resolution mass spectrometry (FAB, [M+H]$^+$) C$_{29}$H$_{31}$N$_2$O$_3$, Calculated value 455.2334, Actual measurement 455.2346.

Example 9: 4-(2-(1,5-Diphenyl-1H-pyrazol-3-yl)-4-fluorophenoxy)butanoic acid

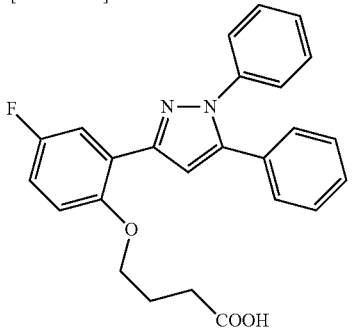

[Formula 27]

The subject compound was prepared in the same manner as Example 1, except for using benzaldehyde instead of 2-chlorobenzaldehyde, and 5'-fluoro-2'-methoxyacetophenone instead of 2'-methoxyacetophenone in Step 1.

$^1$H NMR (400 MHz, CDCl$_3$): δ=7.75 (dd, J=9.6, 3.2 Hz, 1H), 7.37-7.27 (m, 11H), 7.01-6.97 (m, 2H), 6.92 (dd, J=8.8, 4.4 Hz, 1H), 4.12 (t, J=6.0 Hz, 2H), 2.61 (t, J=7.2 Hz, 2H), 2.23-2.17 (m, 2H).

High resolution mass spectrometry (FAB, [M+H]$^+$) C$_{25}$H$_{22}$FN$_2$O$_3$, Calculated value 417.1614, Actual measurement 417.1597.

Example 10: 4-(2-(5-(2-Chlorophenyl-1-phenyl-1H-pyrazol-3-yl)-4-fluorophenoxy)butanoic acid

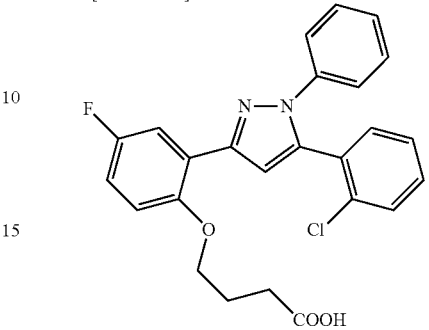

[Formula 28]

The subject compound was prepared in the same manner as Example 1, except for using 5'-fluoro-2'-methoxyacetophenone instead of 2'-methoxyacetophenone in Step 1.

$^1$H-NMR (300 MHz, CDCl$_3$) δ [ppm]: 7.82 (1H, dd, J=9.6, 3.1 Hz), 7.42 (1H, br-d, J=8.2 Hz), 7.34-7.21 (8H, overlapped), 7.05 (1H, s), 6.99 (1H, ddd, J=9.0, 7.6, 3.1 Hz), 6.91 (1H, dd, J=9.1, 4.6 Hz), 4.11 (2H, t, J=6.1 Hz), 2.60 (2H, t, J=7.3 Hz), 2.18 (2H, quin, J=6.7 Hz).

$^{13}$C-NMR (150 MHz, CDCl$_3$) δ [ppm]; 176.6, 158.1, 156.6, 152.3 (d, J=1.8 Hz), 147.8 (d, J=1.8 Hz), 140.4, 139.9, 134.0, 132.2, 130.2 (d, J=6.8 Hz), 130.0, 128.8 (2C), 127.3, 126.7, 124.2 (2C), 123.5 (d, J=7.9 Hz), 115.4 (d, J=24.7 Hz), 115.1 (d, J=23.1 Hz), 113.6 (d, J=8.0 Hz), 110.7, 67.7, 30.4, 24.6.

High resolution mass spectrometry (ESI-TOF-MS, [M−H]$^-$) C$_{25}$H$_{19}$C$_{11}$F$_1$N$_2$O$_3$, Calculated value 449.10682. Actual measurement 449.10312.

Chemical purity: >99% (area % of reverse phase HPLC, detected UV wavelength: 254 nm).

Example 11: 4-(2-(5-(2-chlorophenyl)-1-(4-isopropylphenyl)-1H-pyrazol-3-yl)-4-fluorophenoxy)butanoic acid

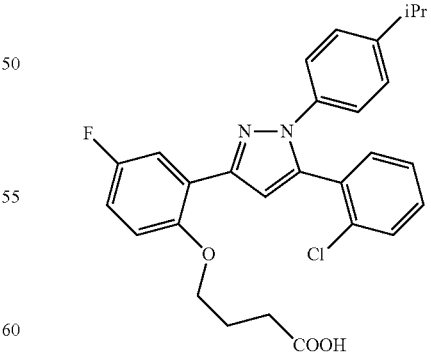

[Formula 29]

The subject compound was prepared in the same manner as Example 1, except for using 5'-fluoro-2'-methoxyacetophenone instead of 2'-methoxyacetophenone in Step 1, and 4-isopropylphenylhydrazine instead of phenylhydrazine in Step 2.

¹H-NMR (300 MHz, CDCl₃) δ [ppm]; 7.81 (1H, dd, J=9.7, 3.1 Hz), 7.43 (1H, br-d, J=8.1 Hz), 7.34-7.21 (5H, overlapped), 7.13 (2H, br-d, J=8.5 Hz), 7.03 (1H, s), 6.98 (1H, ddd, J=9.1, 7.5, 3.1 Hz), 6.91 (1H, dd, J=9.0, 4.6 Hz), 4.11 (2H, t, J=6.1 Hz), 2.88 (1H, sept, J=6.9 Hz), 2.60 (2H, t, J=7.2 Hz), 2.18 (2H, quin, J=6.6 Hz), 1.21 (6H, d, J=6.9 Hz).

¹³C-NMR (150 MHz, CDCl₃) δ [ppm]; 175.8, 158.1, 156.6, 152.2, 148.1, 147.5, 140.3, 137.6, 134.0, 132.2, 130.3, 130.1, 130.0, 126.8 (2C), 126.7, 124.1 (2C), 115.4 (d, J=24.4 Hz), 115.0 (d, J=23.1 Hz), 113.6 (d, J=8.2 Hz), 110.4, 67.6, 33.7, 30.3, 24.6, 23.9 (2C).

High resolution mass spectrometry (ESI-TOF-MS, [M−H]⁻) $C_{28}H_{25}Cl_1F_1N_2O_3$, Calculated value 491.15377. Actual measurement 491.15054.

Chemical purity: >99% (area % of reverse phase HPLC, detected UV wavelength: 254 nm).

Example 12: 4-(2-(5-(2-Methylphenyl)-1-phenyl-1H-pyrazol-3-yl)-phenoxy)butanoic acid

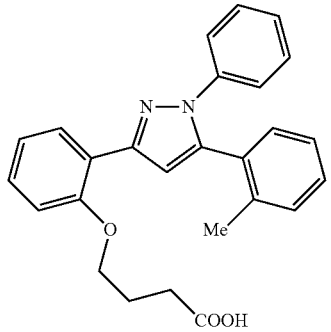

[Formula 30]

The subject compound was prepared in the same manner as Example 1, except for using 2-methylbenzaldehyde instead of 2-chlorobenzaldehyde in Step 1.

¹H-NMR (300 MHz, CDCl₃) δ [ppm]: 8.04 (1H, dd, J=7.7, 1.7 Hz), 7.34-7.17 (10H, overlapped), 7.06 (1H, td, J=7.5, 1.0 Hz), 6.99 (1H, br-d, J=8.3 Hz), 6.89 (1H, s), 4.14 (2H, t, J=6.1 Hz), 2.58 (2H, t, J=7.2 Hz), 2.17 (2H, quin, J=6.6 Hz), 2.06 (3H, s).

¹³C-NMR (75 MHz, CDCl₃) δ [ppm]: 177.2, 156.0, 148.9, 142.7, 140.1, 137.2, 130.9, 130.7, 130.4, 129.24, 129.19, 128.9, 128.7 (2C), 126.9, 125.8, 123.9 (2C), 122.1, 121.1, 112.4, 110.0, 66.8, 30.6, 24.6, 20.0.

High resolution mass spectrometry (ESI-TOF-MS, [M−H]⁻) $C_{26}H_{23}N_2O_3$, Calculated value 411.17087. Actual measurement 411.16706.

Chemical purity: >99% (area % of reverse phase HPLC, detected UV wavelength: 254 nm).

Example 13: 4-(2-(5-(2-Bromophenyl)-1-(4-isopropylphenyl)-1H-pyrazol-3-yl)-4-fluorophenoxy)butanoic acid

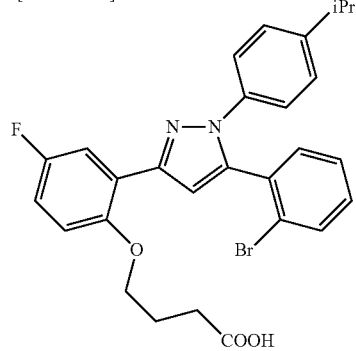

[Formula 31]

The subject compound was prepared in the same manner as Example 1, except for using 5'-fluoro-2'-methoxyacetophenone instead of 2'-methoxyacetophenone and 2-bromobenzaldehyde instead of 2-chlorobenzaldehyde in Step 1, and 4-isopropylphenylhydrazine instead of phenylhydrazine in Step 2.

¹H-NMR (300 MHz, CDCl₃) δ [ppm]; 7.82 (1H, dd, J=9.7, 3.1 Hz), 7.62 (1H, br-d, J=7.6 Hz), 7.29-7.21 (5H, overlapped), 7.13 (2H, br-d, J=8.5 Hz), 7.02 (1H, s), 6.98 (1H, ddd, J=9.0, 7.6, 3.1 Hz), 6.91 (1H, dd, J=9.1, 4.7 Hz), 4.11 (2H, t, J=6.1 Hz), 2.87 (1H, sept, J=6.9 Hz), 2.61 (2H, t, J=7.2 Hz), 2.18 (2H, quin, J=6.6 Hz), 1.21 (6H, d, J=6.9 Hz).

¹³C-NMR (150 MHz, CDCl₃) δ [ppm]; 176.0, 158.1, 156.6, 152.2, 148.1, 147.4, 141.8, 137.5, 133.1, 132.42, 132.35, 130.2 (2C), 127.2, 126.8 (2C), 124.2 (2C), 115.4 (d, J=24.4 Hz), 115.0 (d, J=23.1 Hz), 113.6 (d, J=8.5 Hz), 110.4, 67.7, 33.7, 30.3, 24.6, 23.8 (2C).

High resolution mass spectrometry (ESI-TOF-MS, [M−H]⁻) $C_{28}H_{25}Br_1F_1N_2O_3$, Calculated value 535.10326, Actual measurement 535.10054.

Chemical purity: >99% (area % of reverse phase HPLC, detected UV wavelength: 254 nm).

Example 14: (S)-4-(2-(5-(2-Chlorophenyl)-1-phenyl-1H-pyrazol-3-yl)-phenoxy)-2-methylbutanoic acid

[Step 1] Preparation of (S)-4-benzyl-3-(4-(benzyloxy)butanoyl)oxazolidin-2-one

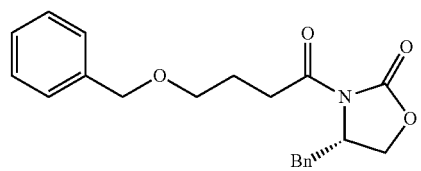

[Formula 32]

4-Benzyloxybutanoic acid (2.50 g, 12.9 mmol, 1.0 eq), (S)-4-benzyl-2-oxazolidine (4.56 g, 25.7 mmol, 2.0 eq), 4-dimethylaminopyridine (1.57 g, 12.9 mmol, 1, 0 eq) were dissolved in dry dichloromethane (100 ml), to which diisopropylcarbodiimide (2.19 ml, 14.2 mmol, 1.1 eq) was added dropwise under an argon atmosphere at 0° C., and the mixture was stirred at room temperature overnight. The reaction mixture was added to a saturated sodium hydrogen carbonate aqueous solution, the mixture was extracted with dichloromethane, and the organic phase was dried with anhydrous magnesium sulfate and concentrated. The residue was purified using silica gel column chromatography (silica gel 60, eluant: n-hexane/ethyl acetate=1:1 (v/v)), to obtain the subject compound (3.67 g, yield: 80.6%) as a colorless oil-like substance.

$^1$H-NMR (300 MHz, CDCl$_3$) δ [ppm]: 7.35-7.26 (m, 8H), 7.19 (d, J=6.9 Hz, 2H), 4.64-4.56 (m, 1H), 4.51 (s, 2H), 4.14-4.07 (m, 2H), 3.58 (t, J=6.0 Hz, 2H), 3.27 (dd, J=13.8, 3.3 Hz, 1H), 3.07 (t, J=6.9 Hz, 2H), 2.69 (dd, J=13.2, 9.3 Hz, 1H), 2.04 (quintet, J=6.6 Hz, 2H).

[Step 2] Preparation of (S)-4-benzyl-3-((S)-4-(benzyloxy)-2-methylbutanoyl)oxazolidin-2-one

[Formula 33]

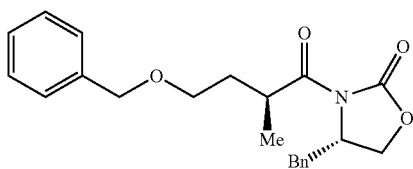

(S)-4-Benzyl-3-(4-(benzyloxy)butanoyl)oxazolidin-2-one (1.39 g, 3.94 mmol, 1.0 eq) was dissolved in dry tetrahydrofuran (40 ml), and sodium bis(trimethylsilyl)amide (1.0 mol/L tetrahydrofuran solution, 4.73 ml, 4.73 mmol, 1.2 eq) was added dropwise. The reaction mixture was stirred at −50° C. for 5 min, and at −15° C. for 15 min. Then, it was cooled to −50° C. again, and iodomethane (1.23 ml, 19.7 mmol, 5.0 eq) dissolved in dry tetrahydrofuran (4 ml) was added dropwise. The temperature of the reaction mixture was raised at a rate of 5° C. per 15 min., and was stirred at −5° C. for 5 hours. The reaction was quenched by a saturated ammonium chloride aqueous solution, the reaction mixture was extracted with ethyl acetate, and the organic phase was washed with saturated brine, dried with anhydrous magnesium sulfate and concentrated. The residue was purified using silica gel column chromatography (silica gel 60, eluant: n-hexane/ethyl acetate=3:1 (v/v)), to obtain the subject compound (1.15 g, yield: 79%) as a pale yellow, oil-like substance.

$^1$H-NMR (300 MHz, CDCl$_3$) δ [ppm]: 7.34-7.19 (m, 8H), 7.17-7.14 (m, 2H), 4.49-4.36 (m, 3H), 4.00-3.88 (m, 2H), 3.73 (t, J=8.7 Hz, 1H), 3.61-3.50 (m, 2H), 3.20 (dd, J=13.5, 3.6 Hz, 1H), 2.70 (dd, J=13.2 Hz, 1H), 2.24-2.12 (m, 1H), 1.79-1.70 (m, 1H), 1.24 (d, J=6.9 Hz, 3H).

$^{13}$C-NMR (75 MHz, CDCl$_3$) δ [ppm]: 177.10, 153.26, 138.51, 135.42, 129.40, 128.84, 128.27, 127.59, 127.53, 127.23, 72.84, 68.47, 65.83, 55.21, 37.98, 35.14, 33.63, 18.08.

[Step 3] Preparation of (S)-4-benzyl-3-((S)-4-hydroxy-2-methylbutanoyl)oxazolidin-2-one

[Formula 34]

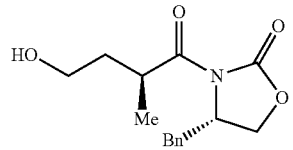

(S)-4-Benzyl-3-((S)-4-(benzyloxy)-2-methylbutanoyl)oxazolidin-2-one (1.06 g, 2.90 mmol, 1.0 eq) was dissolved in ethanol (10 ml), to which paradium carbon (0.10 g) was added under an argon atmosphere, and the flask was filled with hydrogen using a balloon. The reaction mixture was stirred at room temperature under a hydrogen atmosphere for 12 hours, filtered through Celite, and washed with ethyl acetate. The filtrate was concentrated and the residue was purified using silica gel column chromatography (silica gel 60, eluant: n-hexane/ethyl acetate=1:1 v/v) to obtain the subject compound (0.779 g, yield: 97.0%) as a pale yellow liquid.

$^1$H-NMR (300 MHz, CDCl$_3$) δ [ppm]: 7.38-7.28 (m, 3H), 7.20-7.17 (m, 2H), 5.18 (br-s, 1H), 4.48 (t, J=8.1 Hz, 1H), 4.35 (td, J=8.7, 3.0 Hz, 1H), 4.23-4.05 (m, 3H), 2.94-2.81 (m, 2H), 2.65-2.54 (m, 1H), 2.49-2.39 (m, 1H), 2.00-1.86 (m, 1H), 1.29 (d, J=6.9 Hz, 3H).

$^{13}$C-NMR (75 MHz, CDCl$_3$) δ [ppm]: 180.17, 158.96, 135.97, 129.07, 128.97, 127.34, 69.71, 66.27, 53.81, 41.55, 34.18, 30.74, 15.22.

High resolution mass spectrometry (ESI-TOF-MS, [M+H]$^+$) C$_{15}$H$_{20}$NO$_4$, Calculated value 278.1392, Actual measurement 278.1389.

[Step 4] Preparation of (S)-4-benzyl-3-((S)-4-(2-(5-(2-chlorophenyl)-1-phenyl-1H-pyrazol-3-yl)phenoxy)-2-methylbutanoyl)oxazolidin-2-one

[Formula 35]

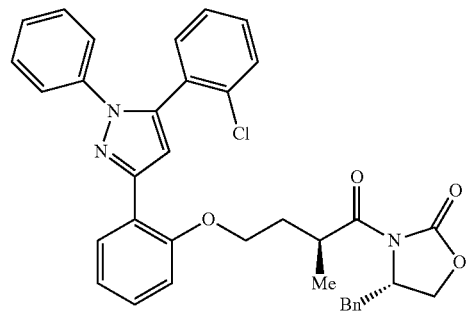

5-(2-Chlorophenyl)-3-(2-hydroxyphenyl)-1-phenyl-1H-pyrazole (0.300 g, 0.865 mmol, 1.0 eq), (S)-4-benzyl-3-((S)-4-hydroxy-2-methylbutanoyl)oxazolidin-2-one (0.252 g, 0.908 mmol, 1.05 eq), triphenylphosphene (0.238 g, 0.908 mmol, 1.05 eq) were dissolved in dry diethyl ether, to which diisopropyl azodicarboxylate (40% toluene solution, about 1.9 mol/L) was added dropwise under an argon atmosphere at 0° C. The reaction mixture was stirred at room temperature for 3 days and concentrated, and the residue was purified using silica gel column chromatography (silica gel 60, eluant: n-hexane/ethyl acetate=3:1 v/v) to obtain the subject compound (0.321 g, yield: 61.2%) as a colorless oil-like substance.

[α]$^{25}_D$+54.9 (c=1.0, CHCl$_3$)

$^1$H-NMR (300 MHz, CDCl$_3$) δ [ppm]: 8.13 (dd, 7.8, 1.8 Hz, 1H), 7.54-7.48 (m, 1H), 7.40-7.19 (m, 12H), 7.13-7.10 (m, 2H), 7.06 (s, 1H), 7.04 (td, J=3.3, 1.2 Hz, 1H), 6.98 (d, J=8.4 Hz, 1H), 4.50-4.42 (m, 1H), 4.27-4.20 (m, 1H), 4.15-4.07 (m, 1H), 4.04 (dt, J=6.9, 1.5 Hz, 1H), 3.99 (dd, J=9.0, 2.4 Hz, 1H), 3.90 (t, J=8.1 Hz, 1H), 3.16 (dd, J=13.8, 3.3 Hz, 1H), 2.71 (dd, J=13.5, 9.6 Hz, 1H), 2.46-2.34 (m, 1H), 2.08-1.97 (m, 1H), 1.31 (d, J=7.2 Hz, 1H).

$^{13}$C-NMR (75 MHz, CDCl$_3$) δ [ppm]: 176.4, 156.0, 153.0, 148.5, 140.3, 140.1, 135.2, 134.0, 132.4, 130.6, 130.0, 129.8, 129.4, 129.1, 128.8, 128.7, 127.2, 126.9, 126.8, 123.9, 121.8, 121.0, 112.1, 111.0, 66.4, 66.0, 55.1, 37.8, 35.2, 33.2, 18.2.

High resolution mass spectrometry (ESI-TOF-MS, [M+H]$^+$) C$_{36}$H$_{33}$ClN$_3$O$_4$, Calculated value 606.2154, Actual measurement 606.2142.

[Step 5] Purification of (S)-4-(2-(5-(2-chlorophenyl)-1-phenyl-1H-pyrazol-3-yl)-phenoxy)-2-methylbutanoic acid

[Formula 36]

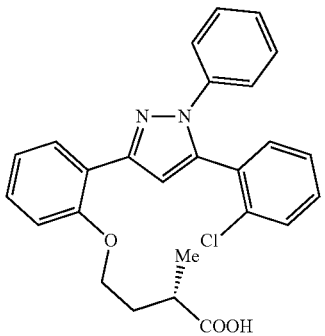

(S)-4-Benzyl-3-((S)-4-(2-(5-(2-chlorophenyl)-1-phenyl-1H-pyrazol-3-yl)phenoxy)-2-methylbutanoyl)oxazolidin-2-one (0.100 g, 0.165 mmol, 1.0 eq) was dissolved in tetrahydrofuran/water (3:1, 2.0 ml), to which was added dropwise at 0° C., a 30% hydrogen peroxide aqueous solution (0.10 ml, 0.89 mmol, 5.4 eq) followed by lithium hydroxide (0.028 g, 0.66 mmol, 4.0 eq) dissolved in water (0.3 ml). The mixture was stirred at 0° C. for 3 hours, and the reaction was quenched by adding sodium thiosulfate (0.1 g) dissolved in water (0.5 ml), then the reaction mixture was acidified by 1 mol/L hydrochloric acid. Tetrahydrofuran was removed by evaporation and the mixture was extracted with ethyl acetate. The organic phase was washed with saturated brine, dried with anhydrous magnesium sulfate and concentrated. The residue was purified using silica gel column chromatography (silica gel 60, eluant: n-hexane/ethyl acetate=3:1 v/v) to obtain the subject compound (54.5 mg, yield: 73.9%) as a colorless amorphous.

[α]$^{25}_D$+47.5 (c=1.0, CHCl$_3$).

$^1$H-NMR (300 MHz, CDCl$_3$) δ [ppm]: 7.93 (dd, J=7.5, 1.8 Hz, 1H), 7.42-7.38 (m, 1H), 7.35-7.21 (m, 9H), 7.05 (td, J=7.5, 1.2 Hz, 1H), 7.01-6.98 (m, 2H), 4.26-4.19 (m, 1H), 4.08-4.00 (m, 1H), 2.94-2.82 (m, 1H), 2.17-2.07 (m, 1H), 2.05-1.98 (m, 1H), 1.10 (d, J=6.9 Hz, 3H).

$^{13}$C-NMR (75 MHz, CDCl$_3$) δ [ppm]: 180.3, 156.0, 149.0, 140.4, 139.7, 133.9, 132.2, 130.2, 130.04, 129.99, 129.5, 129.4, 128.9 (2C), 127.4, 126.7, 124.5 (2C), 121.7, 121.1, 112.4, 110.3, 65.6, 36.4, 33.3, 17.0.

High resolution mass spectrometry (ESI-TOF-MS, [M+H]$^+$) C$_{26}$H$_{24}$Cl$_1$N$_2$O$_3$, Calculated value 447.14755. Actual measurement 447.14591.

Example 15: (R)-4-(2-(5-(2-Chlorophenyl)-1-phenyl-1H-pyrazol-3-yl)-phenoxy)-2-methylbutanoic acid

[Step 1] Preparation of (R)-4-benzyl-3-(4-(benzyloxy)butanoyl)oxazolidin-2-one

[Formula 37]

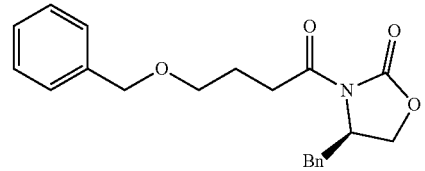

4-Benzyloxybutanoic acid (2.50 g, 12.9 mmol, 1.0 eq), (R)-4-benzyl-2-oxazolidinone (4.56 g, 25.7 mmol, 2.0 eq), and 4-dimethylaminopyridine (1.57 g, 12.9 mmol, 1, 0 eq) were dissolved in dry dichloromethane (100 ml), and diisopropylcarbodiimide (2.19 ml, 14.2 mmol, 1.1 eq) was added dropwise under an argon atmosphere at 0° C., then the mixture was stirred at room temperature overnight. The reaction mixture was added to a saturated sodium hydrogen carbonate aqueous solution, the mixture was extracted with dichloromethane, and the organic phase was dried using anhydrous magnesium sulfate and concentrated. The residue was purified using silica gel column chromatography (silica gel 60, eluant: n-hexane/ethyl acetate=1:1 v/v) to obtain the subject compound (3.76 g, yield: 82.7%) as a colorless oil-like substance.

$^1$H-NMR (300 MHz, CDCl$_3$) δ [ppm]: 7.35-7.26 (m, 8H), 7.19 (d, J=6.6 Hz, 2H), 4.64-4.56 (m, 1H), 4.51 (s, 2H), 4.13-4.06 (m, 2H), 3.58 (t, J=6.0 Hz, 2H), 3.27 (dd, J=13.5, 3.3 Hz, 1H), 3.07 (t, J=7.2 Hz, 2H), 2.69 (dd, J=13.2, 9.3 Hz, 1H), 2.04 (quintet, J=6.9 Hz, 2H).

[Step 2] Preparation of (R)-4-benzyl-3-((R)-4-(benzyloxy)-2-methylbutanoyl)oxazolidin-2-one

[Formula 38]

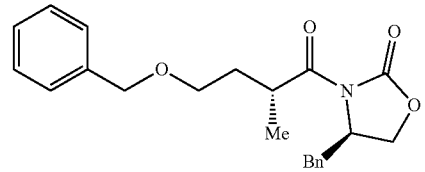

(R)-4-Benzyl-3-(4-(benzyloxy)butanoyl)oxazolidin-2-one (0.750 g, 2.12 mmol, 1.0 eq) was dissolved in dry tetrahydrofuran (20 ml), and sodium bis(trimethylsilyl)amide (1.0 mol/L tetrahydrofuran solution, 2.55 ml, 2.55 mmol, 1.2 eq) was added dropwise under an argon atmosphere at −50° C. The mixture was stirred at −50° C. for 5 min., and at −15° C. for 15 min. Then, the mixture was cooled to −50° C. again, and iodomethane (0.66 ml, 11 mmol, 5.0 eq) dissolved in dry tetrahydrofuran (2 ml) was added dropwise. The temperature of the reaction mixture was raised at a rate of 5° C. per 15 min. and the mixture was stirred at −5° C. for 5 hours. The reaction was quenched by a saturated ammonium chloride aqueous solution, the mixture was extracted with ethyl acetate, and the organic phase was washed with saturated brine, dried using anhydrous magnesium sulfate, and concentrated. The residue was purified using silica gel column chromatography (silica gel 60, eluant: n-hexane/ethyl acetate=3:1 v/v) to obtain the subject compound (0.62 g, yield: 80%) as a pale yellow, oil-like substance.

$^1$H-NMR (300 MHz, CDCl$_3$) δ [ppm]: 7.34-7.19 (m, 8H), 7.17-7.14 (m, 2H), 4.49-4.36 (m, 3H), 3.73 (t, J=8.1 Hz, 1H), 3.61-3.50 (m, 2H), 3.20 (dd, J=13.2, 3.3 Hz, 1H), 2.70 (dd, J=13.2, 9.6 Hz, 1H), 2.24-2.12 (m, 1H), 1.79-1.70 (m, 1H), 1.24 (d, J=6.6 Hz, 3H).

$^{13}$C-NMR (75 MHz, CDCl$_3$) δ [ppm]: 177.11, 153.27, 138.52, 135.43, 129.41, 128.85, 128.28, 127.64, 127.54, 127.23, 72.84, 68.48, 65.84, 55.22, 37.99, 35.15, 33.64, 18.08.

[Step 3] Preparation of (R)-4-benzyl-3-((R)-4-hydroxy-2-methylbutanoyl)oxazolidin-2-one

[Formula 39]

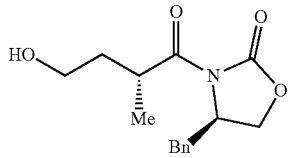

(R)-4-Benzyl-3-((R)-4-(benzyloxy)-2-methylbutanoyl) oxazolidin-2-one (0.597 g, 1.63 mmol, 1.0 eq) was dissolved in ethanol (5.0 ml), and paradium carbon (0.06 g) was added to the solution under an argon atmosphere, then the flask was filled with hydrogen using a balloon. The reaction mixture was stirred under a hydrogen atmosphere at room temperature for 12 hours, filtered through Celite, and washed with ethyl acetate. The filtrate was concentrated and the residue was purified using silica gel column chromatography (silica gel 60, eluant: n-hexane/ethyl acetate=1:1 v/v) to obtain the subject compound (0.388 g, yield: 86.1%) as a pale yellow liquid.

$^1$H-NMR (300 MHz, CDCl$_3$) δ [ppm]: 7.37-7.28 (m, 3H), 7.19-7.17 (m, 2H), 5.26 (br-s, 1H), 4.48 (t, J=8.1 Hz, 1H), 4.35 (td, J=8.7, 2.4 Hz, 1H), 4.23-4.05 (m, 3H), 2.94-2.82 (m, 2H), 2.68-2.54 (m, 1H), 2.49-2.39 (m, 1H), 2.00-1.86 (m, 1H), 1.29 (d, J=6.9 Hz, 3H).

$^{13}$C-NMR (75 MHz, CDCl$_3$) δ [ppm]: 180.18, 159.02, 135.96, 129.07, 128.97, 127.32, 69.70, 66.27, 53.80, 41.53, 34.18, 30.73, 15.21.

High resolution mass spectrometry (ESI-TOF-MS, [M+H]$^+$) C$_{15}$H$_{20}$NO$_4$, Calculated value 278.1392, Actual measurement 278.1387.

[Step 4] Preparation of (R)-4-benzyl-3-((R)-4-(2-(5-(2-chlorophenyl)-1-phenyl-1H-pyrazol-3-yl)phenoxy)-2-methylbutanoyl)oxazolidin-2-one

[Formula 40]

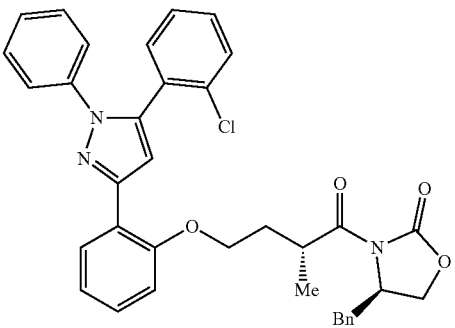

5-(2-Chlorophenyl)-3-(2-hydroxyphenyl)-1-phenyl-1H-pyrazole (0.300 g, 0.865 mmol, 1.0 eq), (R)-4-benzyl-3-((R)-4-hydroxy-2-methylbutanoyl)oxazolidin-2-one (0.252 g, 0.908 mmol, 1.05 eq), and triphenylphosphine (0.238 g, 0.908 mmol, 1.05 eq) were dissolved in dry diethylether, and diisopropyl azodicarboxylate (40% toluene solution, about 1.9 mol/L) was added dropwise under an argon atmosphere at 0° C. The reaction mixture was stirred at room temperature for 3 days, and concentrated, and the residue was purified using silica gel column chromatography (silica gel 60, eluant n-hexane/ethyl acetate=3:1 v/v) to obtain the subject compound (0.323 g, yield: 61.6%) as a colorless oil-like substance.

[α]$^{25}_D$-53.3 (c=1.0, CHCl$_3$).

$^1$H-NMR (300 MHz, CDCl$_3$) δ [ppm]: 8.13 (dd, J=7.5, 1.8 Hz, 1H), 7.52-7.49 (m, 1H), 7.40-7.19 (m, 12H), 7.13-7.10 (m, 2H), 7.06-7.00 (m, 2H), 6.98 (d, J=8.4 Hz, 1H), 4.50-4.42 (m, 1H), 4.27-4.20 (m, 1H), 4.15-4.07 (m, 1H), 4.04 (dt, J=6.9, 1.8 Hz, 1H), 3.99 (dd, J=9.0, 2.4 Hz, 1H), 3.90 (t, J=8.1 Hz, 1H), 3.16 (dd, J=13.5, 3.3 Hz, 1H), 2.71 (dd, J=13.5, 9.6 Hz, 1H), 2.46-2.34 (m, 1H), 2.08-1.97 (m, 1H), 1.31 (d, J=7.2 Hz, 1H).

$^{13}$C-NMR (75 MHz, CDCl$_3$) δ [ppm]: 176.4, 156.0, 153.0, 148.5, 140.3, 140.1, 135.2, 134.0, 132.4, 130.0, 129.8, 129.4, 129.1, 128.9, 128.7, 127.2, 126.9, 126.8, 123.9, 121.8, 121.0, 112.1, 111.0, 66.4, 66.0, 55.1, 37.8, 35.2, 33.2, 18.2.

High resolution mass spectrometry (ESI-TOF-MS, [M+H]$^+$) C$_{36}$H$_{33}$ClN$_3$O$_4$, Calculated value 606.2154, Actual measurement 606.2178.

[Step 5] Preparation of (R)-4-(2-(5-(2-chlorophenyl)-1-phenyl-1H-pyrazol-3-yl)-phenoxy)-2-methylbutanoic acid

[Chem. 41]

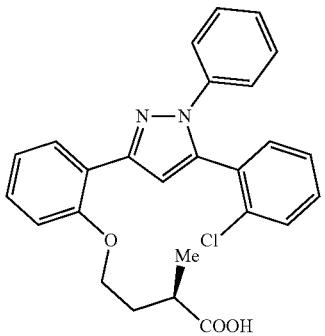

(R)-4-Benzyl-3-((R)-4-(2-(5-(2-chlorophenyl)-1-phenyl-1H-pyrazol-3-yl)phenoxy)-2-methylbutanoyl)oxazolidin-2-one (0.140 g, 0.231 mmol, 1.0 eq) was dissolved in tetrahydrofuran/water (3:1, 2.8 ml), and to this solution was added dropwise a 30% hydrogen peroxide aqueous solution (0.14 ml, 1.25 mmol, 5.4 eq) at 0° C. followed by lithium hydroxide (0.039 g, 0.92 mmol, 4.0 eq) dissolved in water (0.4 ml). The mixture was stirred at 0° C. for 3 hours, the reaction was quenched by adding sodium thiosulfate (0.14 g) dissolved in water (0.7 ml), and the reaction mixture was acidified with a 1 mol/L hydrochloric acid solution. Tetrahydrofuran was removed by evaporation, and the remaining mixture was extracted with ethyl acetate. The organic phase was washed with saturated brine, dried with anhydrous magnesium sulfate and concentrated. The residue was purified using silica gel column chromatography (silica gel 60, eluant: n-hexane/ethyl acetate=3:1 v/v) to obtain the subject compound (91.0 mg, yield: 88.2%) as a colorless amorphous.

$[\alpha]^{25}_D$-48.2 (c=1.0, CHCl$_3$).

$^1$H-NMR (300 MHz, CDCl$_3$) δ [ppm]; 7.96 (dd, J=7.5, 1.5 Hz, 1H), 7.39 (dd, J=10.8, 1.2 Hz, 1H), 7.34-7.20 (m, 9H), 7.05 (td, J=7.2, 0.9 Hz, 1H), 6.99-6.97 (m, 2H), 4.24-4.17 (m, 1H), 4.09-4.01 (m, 1H), 2.21-2.10 (m, 1H), 2.03-1.92 (m, 1H), 1.13 (d, J=6.9 Hz, 3H).

$^{13}$C-NMR (75 MHz, CDCl$_3$) δ [ppm]; 180.8, 156.0, 148.9, 140.3, 139.8, 133.9, 132.2, 130.14, 130.12, 130.0, 129.4, 129.4, 128.8 (2C), 127.3, 126.7, 124.4 (2C), 121.7, 121.1, 112.4, 110.5, 65.6, 36.4, 33.2, 17.0.

High resolution mass spectrometry (ESI-TOF-MS, [M+H]$^+$) C$_{26}$H$_{24}$Cl$_1$N$_2$O$_3$, Calculated value 447.14755, Actual measurement 447.14874.

Comparative Example 1: 4-(2-(1-(2-Methoxyphenyl)-5-phenyl-H-pyrazol-3-yl)phenoxy)butanoic acid

[Step 1] Preparation of ((E)-1-(2-methoxyphenyl)-3-phenylprop-2-en-1-one

[Formula 42]

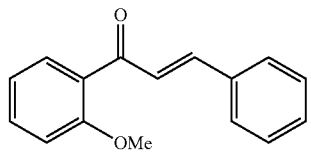

2'-Methoxyacetophenone (1.09 g, 6.60 mmol) and 10% potassium hydroxide aqueous solution (80 mL, 142 mmol) were dissolved in ethanol (15 mL), and stirred at 0° C. for 30 min. before adding benzaldehyde (0.800 mL, 7.92 mmol) dropwise, and the mixture was stirred at room temperature for about 2 days. Ethanol was removed by evaporation using an evaporator, and the remaining mixture was extracted 4 times with ethyl acetate (30 mL), after which the extract was dried with magnesium sulfate, and the filtered solution was concentrated. The residue was purified using silica gel column chromatography (silica gel 60, eluant: ethyl acetate/hexane=1:7 (v/v)) to obtain the subject compound (1.52 mg, 6.36 mmol, yield: 96%) as a yellow, oil-like substance.

$^1$H NMR (400 MHz, CDCl$_3$): δ: 7.64 (d, J=4.8 Hz, 1H), 7.61-7.57 (m, 3H), 7.48 (ddd, J=15.2, 15.2, 2.0 Hz, 1H), 7.41-7.35 (m, 4H), 7.05 (dd, J=6.4, 6.4 Hz, 1H), 7.01 (d, J=8.5 Hz, 1H), 3.91 (s, 3H).

[Step 2] Preparation of 3-(2-(benzyloxy)phenyl)-1-(2-methoxyphenyl)-5-phenyl-1H-pyrazole

[Formula 43]

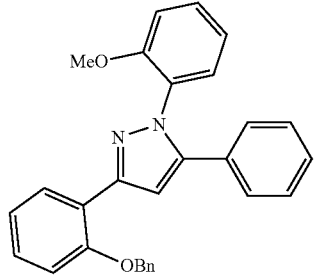

(E)-1-(2-Methoxyphenyl)-3-phenylprop-2-en-1-one (300 mg, 1.26 mmol) was dissolved in dichloromethane (30 mL), and boron tribromide (1.0 mol/L dichloromethane solution, 2.52 mL) was added at −78° C. using a syringe under an argon atmosphere. The reaction mixture was stirred at −78° C. for 30 min., then brought to room temperature to be stirred for 7 hours. The reaction solution was released into saturated brine (150 mL), extracted 4 times with ethyl acetate (30 mL), and the extract was washed with saturated brine. The washed extract was dried with magnesium sulfate, and the filtered solution was concentrated. The residue was dissolved in acetone, benzylbromide (239 μL, 2.01 mmol) was added to the solution using a syringe under the presence of potassium carbonate (367 mg, 2.66 mmol), and the mixture was subjected to reflux under heating for 11 hours. Acetone was removed by evaporation, and the mixture was extracted 4 times with ethyl acetate (30 mL), and washed with saturated brine. The extract was dried using magnesium sulfate, and the filtered solution was concentrated. The residue was purified using silica gel column chromatography (silica gel 60, eluant: ethyl acetate/hexane=1:7 (v/v)) to obtain the subject compound (E)-1-(2-(benzyloxy)phenyl)-3-phenylprop-2-en-1-one (287 mg, 0.91 mmol, yield: 69% (2 steps)). The obtained compound was dissolved in ethanol (20 mL) with 2-methoxyphenylhydrazine chloric acid salt (238 mg, 1.37 mmol), and to this solution was added acetic acid (2.0 mL). The reaction solution was subjected to reflux under heating for about 20 hours under an argon atmosphere. The solvent was removed by evaporation using an evaporator, the remaining mixture was extracted 4 times with ethyl acetate (30 mL) and dried with magnesium sulfate, and the filtered solution was concentrated. The residue was dissolved in benzene (20 mL) with 2,3-dichloro-5,6-dicyanobenzoquinone (413 mg, 1.82 mmol), and heated at 85° C. for 16 hours. The reaction solution was brought to room temperature and filtered through Celite, and the filtrate was concentrated. The residue was purified using silica gel column chromatography (silica gel 60, eluant: ethyl acetate/hexane=1:10 (v/v)) to obtain the subject compound as a pale yellow amorphous substance (249 mg, 0.570 mmol, yield: 63% (2 steps)).

$^1$H NMR (400 MHz, CDCl$_3$): δ=8.13 (dd, J=8.0, 1.6 Hz, 1H), 7.55-7.53 (m, 3H), 7.55-7.17 (m, 10H), 7.13 (s, 1H), 7.07-7.03 (m, 3H), 6.87 (dd, J=8.4, 1.2 Hz, 1H), 5.23 (s, 2H), 3.43 (s, 3H).

[Step 3] Preparation of 2-(1-(2-methoxyphenyl)-5-phenyl-H-pyrazol-3-yl)phenol

[Formula 44]

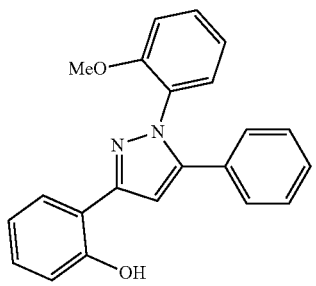

3-(2-(Benzyloxy)phenyl)-1-(2-methoxyphenyl)-5-phenyl-1H-pyrazole (245 mg, 0.570 mmol) was dissolved in ethyl acetate, to which 10% paradium supported active charcoal (49 mg) was added, and the mixture was subjected to 6 hours of catalytic reduction under a 0.3 MPa hydrogen atmosphere. The reaction mixture was filtered through Celite, and the filtrate was concentrated. The residue was purified using silica gel column chromatography (silica gel 60, eluant: ethyl acetate/hexane=1:10 (v/v)) to obtain the subject compound as a colorless amorphous substance (153 mg, 0.447 mmol, yield: 78%).

$^1$H NMR (400 MHz, CDCl$_3$): δ=10.87 (s, 1H), 7.66 (dd, J=8.7, 1.2 Hz, 1H), 7.47 (dd, J=5.9, 1.5 Hz, 1H), 7.41-7.37 (m, 1H), 7.30-7.27 (m, 5H), 7.24-7.21 (m, 1H), 7.08-7.02 (m, 2H), 6.96-6.92 (m, 1H), 6.90-6.88 (m, 2H), 3.45 (s, 3H).

[Step 4] Preparation of methyl 4-(2-(1-(2-methoxyphenyl)-5-phenyl-1H-pyrazol-3-yl)phenoxy)butyrate

[Formula 45]

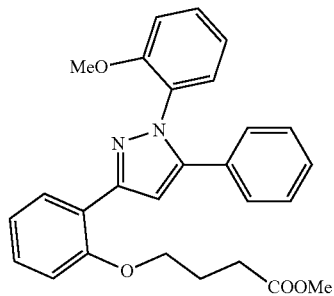

In the same manner as Step 4 of Example 1, 2-(1-(2-methoxyphenyl)-5-phenyl-1H-pyrazol-3-yl)phenol was used to obtain methyl 4-(2-(1-(2-methoxyphenyl)-5-phenyl-1H-pyrazol-3-yl)phenoxy)butyrate (172 mg, 0.388 mmol, 81%) as a colorless substance.

$^1$H NMR (400 MHz, CDCl$_3$): δ=8.09 (dd, J=7.6, 1.6 Hz, 1H), 7.53 (dd, J=7.8, 1.4 Hz, 1H), 7.37-7.33 (m, 1H), 7.30-7.23 (m, 7H), 7.08 (s, 1H), 7.07-6.96 (m, 4H), 6.86 (dd, J=8.4, 1.2 Hz, 1H), 4.15 (t, J=6.0 Hz, 2H), 3.66 (s, 3H), 3.43 (s, 3HH), 2.63 (t, J=7.6 Hz, 2H), 2.27-2.19 (m, 2H).

[Step 5] Preparation of 4-(2-(1-(2-methoxyphenyl)-5-phenyl-1H-pyrazol-3-yl)phenoxy)butanoic acid

[Formula 46]

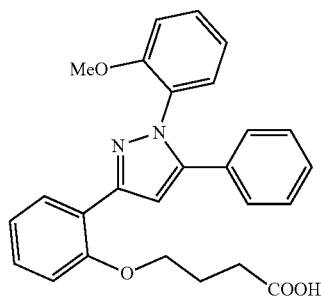

In the same manner as Step 5 of Example 1, methyl 4-(2-(1-(2-methoxyphenyl)-5-phenyl-1H-pyrazol-3-yl)phenoxy)butyrate was used to obtain 4-(2-(1-(2-methoxyphenyl)-5-phenyl-1H-pyrazol-3-yl)phenoxy)butanoic acid (95.0 mg, 0.220 mmol, 58%) as a colorless amorphous substance.

$^1$H NMR (400 MHz, CDCl$_3$): δ=7.83 (dd, J=7.8, 1.8 Hz, 1H), 7.46 (dd, J=7.6, 1.6 Hz, 1H), 7.39-7.24 (m, 7H), 7.05-6.98 (m, 3H), 6.92-6.88 (m, 2H), 4.14 (t, J=6.0 Hz, 2H), 3.49 (s, 3H), 2.56 (t, J=7.2 Hz, 2H), 2.21-2.15 (m, 2H).

High resolution mass spectrometry (FAB, [M+H]$^+$) $C_{26}H_{25}N_2O_4$, Calculated value 429.1814, Actual measurement 429.1827.

Test Example 1: Evaluation of FABP3 Ligand Activity

Adopted for evaluation in the evaluation of FABP3 ligand activity was a fluorescent displacement assay using 1,8-ANS (1-anilino-8-naphthalenesulfonic acid). Fluorescent materials such as 1,8-ANS are characterized by an increase in the fluorescent intensity under a hydrophobic environment. Using this characteristics, 1,8-ANS was made to bind to the hydrophobic ligand binding site of FABP in competition with other compounds, and the ligand activity of each compound against FABP was evaluated by comparing the fluorescence intensities at an excitation wavelength of 355 nm and a measurement wavelength of 460 nm, which are wavelengths used in experiment systems using 1,8-ANS. Ethanol was used as the dilution solvent of the compounds.

A Nunc black plate was used as a 96-well plate for the purpose of measurement, and to each well was added 40 μL of sodium phosphate buffer and a sodium phosphate buffer solution of FABP3 (AVISCERA BIOSCIENCE) (250 nM, 25 μL), and for a blank, 25 μL of sodium phosphate buffer was added. To each well was added as a detection reagent, a 1,8-ANS (ALDRICH) solution (10 μM, ethanol/sodium phosphate buffer solution=1:4 v/v, 25 μL), and ethanol solutions of compounds diluted to different concentrations were added in an amount of 10 μL each (the final ethanol concentration was 15%). The plate was shaken for 10 sec. in the plate reader and incubated for 10 min. at room temperature. Then, it was subjected to fluorescent measurement at an excitation wavelength of 355 nm and a measurement wavelength of 460 nm. Used for measurement was ARVO™ X One by PerkinElmer Japan. The evaluated compounds were evaluated at 4 points, which are $1\times10^{-5}$ M, $1\times10^{-6}$ M, $1\times10^{-7}$ M, $1\times10^{-8}$ M. Further, an oleic acid having affinity with FABP3 and ethanol that was the solvent for the ligand were respectively used as a positive control and a negative control.

Test Example 2: Evaluation of FABP4 Ligand Activity

An evaluation of FABP4 was performed using a fluorescent displacement assay using 1,8-ANS, similar to FABP3. Used in the evaluation of FABP4 was an assay kit (FABP4 Inhibitor/Ligand Screening Assay Kit) available from Cayman Chemical Company. Ethanol was used as a solvent for dissolving the compound, and an arachidonic acid which comes with the kit was used as a positive control. The measurement procedure was performed similarly to the aforementioned FABP3 assay.

Measurement was performed twice each, and the average was adopted as the result. The software, Origin, available from Light Stone was used for calculating $IC_{50}$. The evaluation result is shown in Table 1.

TABLE 1

| Example (Compound) | Structure | FABP3 Ligand activity $IC_{50}$ (μM) | FABP4 Ligand activity $IC_{50}$ (μM) |
|---|---|---|---|
| 1 | (structure) | 0.077 | 0.64 |
| 2 | (structure) | 0.73 | 5.64 |

TABLE 1-continued

| Example (Compound) | Structure | FABP3 Ligand activity IC$_{50}$ (μM) | FABP4 Ligand activity IC$_{50}$ (μM) |
|---|---|---|---|
| 3 | 1-(3,4-dichlorophenyl)-3-[2-(3-carboxypropoxy)phenyl]-5-phenyl-1H-pyrazole | 0.28 | 1.66 |
| 4 | 1-phenyl-3-[2-(3-carboxypropoxy)phenyl]-5-(2-bromophenyl)-1H-pyrazole | 0.052 | 0.36 |
| 5 | 1-(4-isopropylphenyl)-3-[2-(3-carboxypropoxy)phenyl]-5-phenyl-1H-pyrazole | 0.79 | 8.6 |
| 6 | 1-(3-chlorophenyl)-3-[2-(3-carboxypropoxy)phenyl]-5-phenyl-1H-pyrazole | 0.7 | 1.1 |

TABLE 1-continued

| Example (Compound) | Structure | FABP3 Ligand activity IC$_{50}$ (μM) | FABP4 Ligand activity IC$_{50}$ (μM) |
|---|---|---|---|
| 7 | (4-fluorophenyl-pyrazole structure with phenyl and phenoxy-propanoic acid) | 2.0 | 10 |
| 8 | (4-tert-butylphenyl-pyrazole structure with phenyl and phenoxy-butanoic acid) | 1.3 | >10 |
| 9 | (phenyl-pyrazole structure with 4-fluorophenyl and phenoxy-butanoic acid) | 0.51 | >10 |
| Comparative Example 1 | (2-methoxyphenyl-N-pyrazole structure with phenyl and phenoxy-butanoic acid) | >10 | >10 |

Test Example 3: Test of Inhibitory activity against α-synuclein oligomer formation According to a conventional method (Shioda et al., *J Biol Chem* 2014; 289: 18957-18965), PC12 cells were transfected with genes of α-synuclein and FABP3, and the cells were treated with a ligand (compounds of Examples 1 to 3, and Comparative Example 1, 10 µM) in a serum-containing DMEM (containing 10% horse serum, 5% neonatal cow, penicillin/streptomycin) for 16 hours. Samples of such cells in homogenized state were subjected to electrophoresis for 3 hours at 80 mA in a 5 to 13.5% polyacryl amide gel under an unmodified condition, then transferred to the PVDF membrane under a constant voltage of 70 V for 2 hours to be subjected to Western blotting.

The result is shown in FIG. 1. Systems that had a compound of the FABP3 ligand (Examples 1 to 3, 10 µM) added by addition in the culture medium displayed suppression of oligomer formation of α-synuclein, but a system in which the compound of Comparative Example 1 was added displayed no suppression of oligomer formation.

Figure 2:
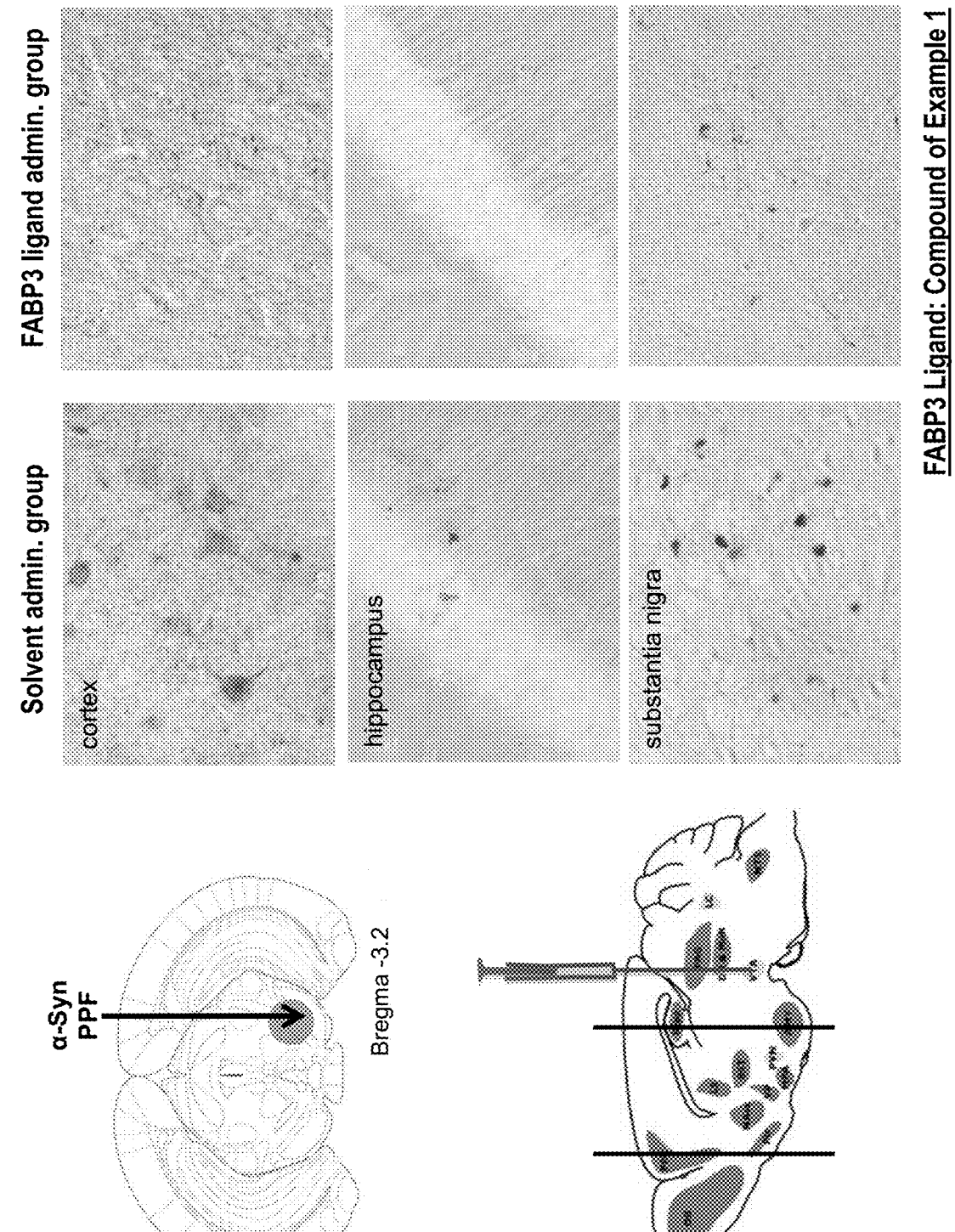
FIG. 2 shows photography of stained brain slices from the prefrontal cortex, dorsal hippocampus, and substantia nigra ventral tegmental area of a mouse subjected to the test of Test Example 4 (using the compound of Example 1). It was confirmed that the FABP3 ligand administered group had less area in which the α-synuclein aggregate, recognized by an anti-α-Syn phospho S129 antibody, was stained relative to the control, a group to which a solvent was administered.

Test Example 4: An In Vivo Test for Confirming α-Synuclein Aggregation Suppression Effect A human α-synuclein recombinant protein (5 µg/L, rPeptide., Bogart, Ga.) in a sterile phosphate buffer saline (pH=7.4) was subjected to incubation for 7 days at a condition of 37° C., 100 rpm, and a fibrillar human α-synuclein (α-Syn PPF, synuclein aggregation) was prepared. After ultrasonic treatment in the sterile phosphate buffer saline (pH=7.4), 10 µg of α-Syn PPF was introduced at a flow rate of 0.2 µL/min. into the right substantia nigra region (3.3 mm back, 1.2 mm to the right and 3.85 mm deep from Bregma) of a 10 week old male C57BL6 N mice (bred at a light/dark cycle of 12 hours (light period: 9:00-21:00; dark period: 21:00-9:00), temperature of 23±1° C., and a humidity of 55±5%) using a microsyringe after fixing the brain in the brain stereotaxic apparatus. From 24 hours after the operation, a solvent (n=3) or FABP3 ligand (compound of Example 1, 1.0 mg/kg, p.o., n=3) was administered once every day for 4 weeks. After each behavioral pharmacology test, the mouse was fixed under perfusion, and 3 brain slices of 50 µm were formed for each region (prefrontal cortex, corpus striatum, dorsal hippocampus, substantia nigra ventral tegmental area) of a single mouse. An anti-phosphorylated α-synuclein (ser129) (α-Syn S129) antibody (Abcam, Cambridge, UK) was used to identify the α-synuclein aggregate by the immunohistochemical staining method. As shown in FIG. 2, suppression of the formation of α-synuclein aggregate (inclusion) was confirmed in the FABP3 ligand administered group.

Figure 3:
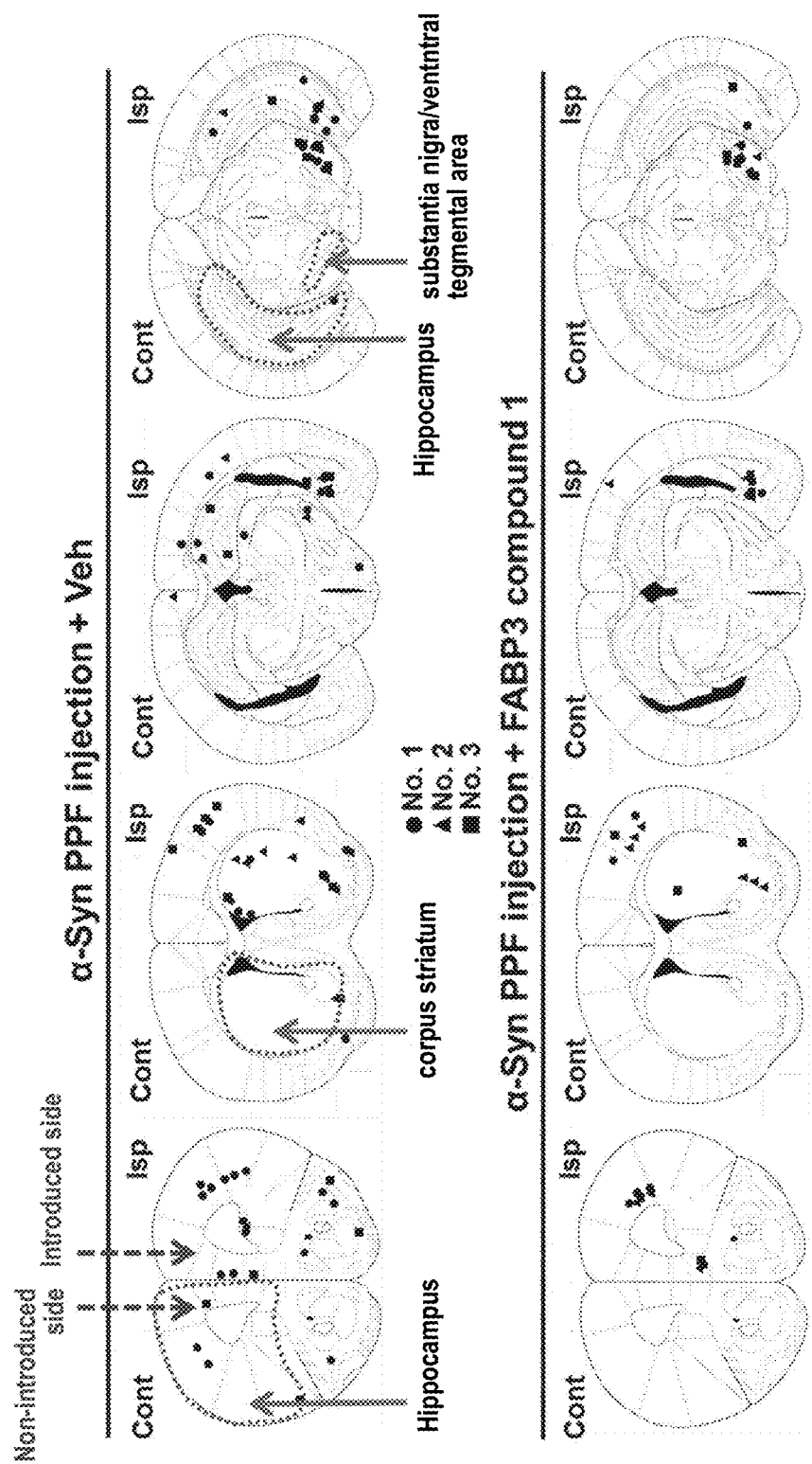
FIG. 3 is a diagram showing accumulated plots of brain regions in which an anti-α-Syn phospho S129 antibody positive cell was observed (both groups n=3). It was confirmed that α-synuclein aggregation was generated on the side on which α-Syn PPF was injected in each individual, and that the aggregation is suppressed in the FABP3 ligand administered group.

FIG. 3 is a diagram accumulatively plotting the brain regions showing α-Syn S129 positive cells (both groups n=3). It was confirmed that an α-synuclein aggregate arose on the side to which an α-Syn PPF was injected of each individual, and that the aggregate was suppressed in a FABP3 ligand administered group.

Figure 4:
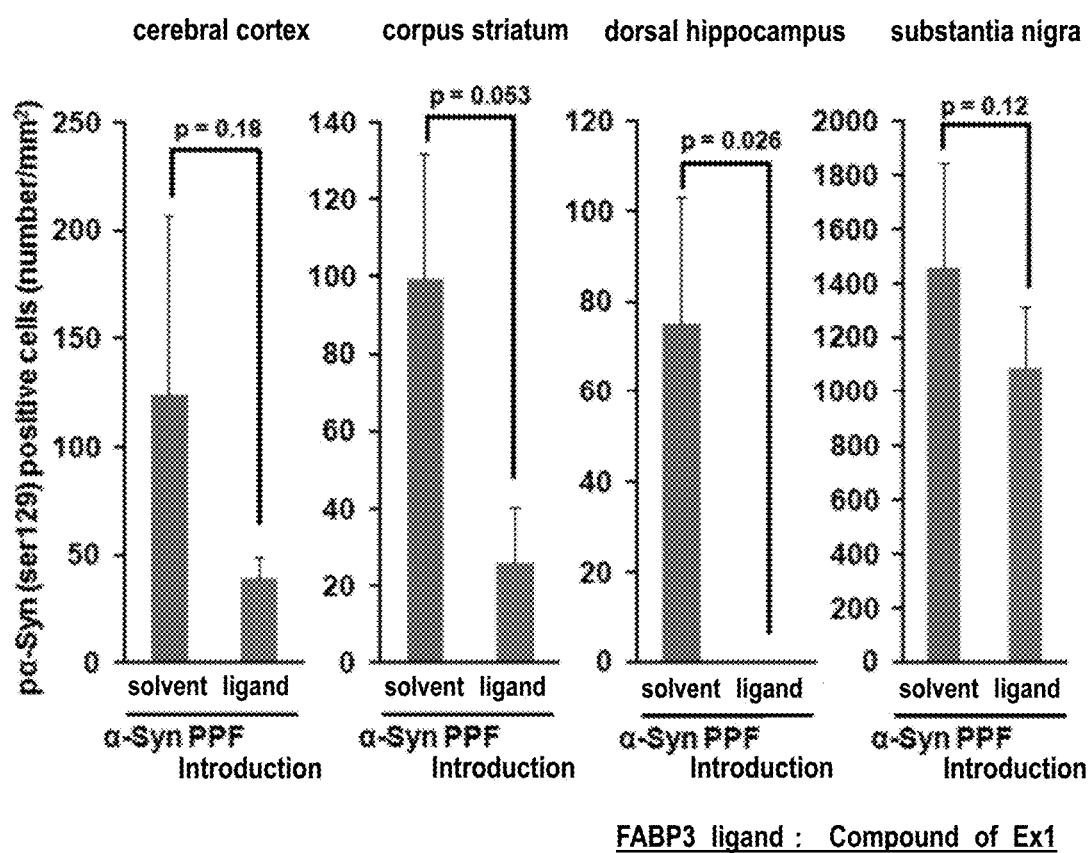
FIG. 4 is a graph showing the result of counting the number of an anti-α-Syn phospho S129 antibody positive cells in the stained brain slice and standardizing the number by the area of the measured brain region (both groups n=3). It was confirmed that the aggregation was regulated in the FABP3 ligand (compound of Example 1) administered group.

The graph of FIG. 4 shows a result of counting the number of α-Syn S129 positive cells in a stained brain slice and standardizing the area of the measured brain region (both groups n=3). It was confirmed that aggregation was suppressed in the FABP3 ligand administered group.

Test Example 5: Evaluation of Motor Function

Figure 5:
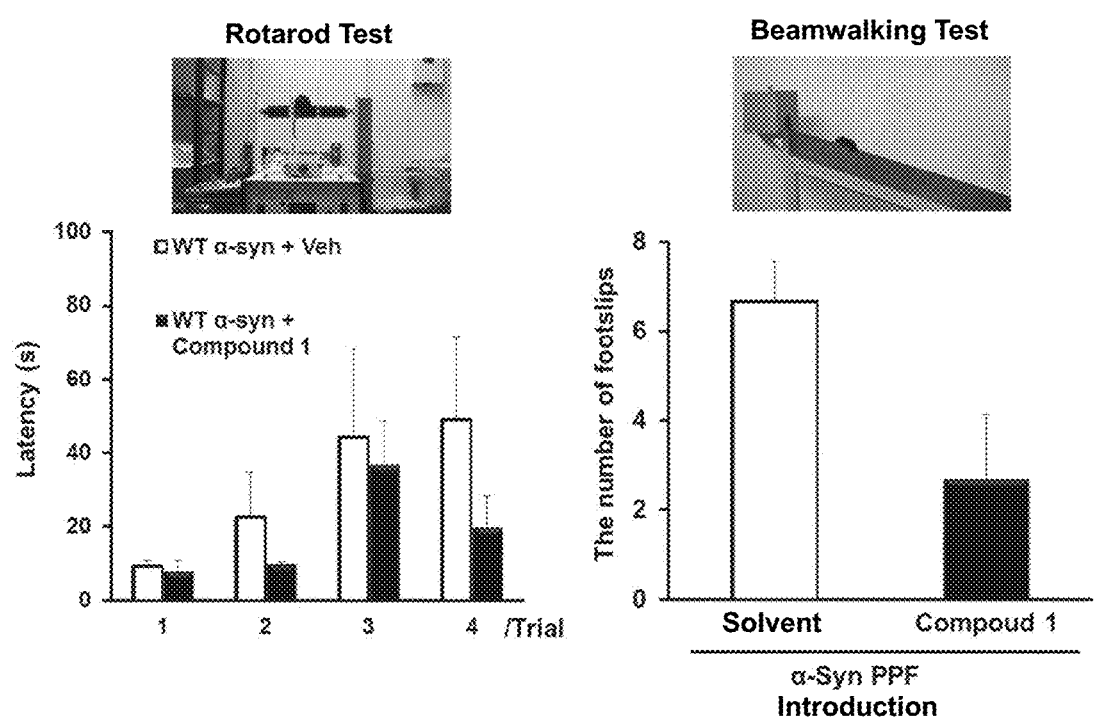
FIG. 5 is a graph showing the result of evaluating the motor function by a rotarod test or a beam walking test in Test Example 5. The vertical axis of the graph showing the result for the rotarod test indicates the time until the mouse falls (sec., Latency). The rotarod test showed a tendency towards shortening of Latency in the ligand administered group. The vertical axis of the graph showing the result of the beam walking test indicates the number of footslips until the mouse reached the goal box. The beam walking test showed a tendency towards decrease in the number of footslips in the ligand administered group.

To an α-Syn PPF-injected mice was administered once every day for 4 weeks a solvent (n=3) or FABP3 ligand (compound of Example 1, 1.0 mg/kg, p.o., n=3), and its motor function was evaluated by a rotarod test and a beam walking test. In a rotarod test, a mouse was put on a roller, and the time until it fell (Latency) was measured while the roller was rotated at a rate of 20 rpm. A tendency towards decrease in the time until the mouse fell was confirmed in the ligand administered group. In a beam walking test, a mouse was put on a thin board and made walk on that board, and the number of footslips until the mouse reached the goal box was counted. The result is shown in FIG. 5. In this beam walking test, a tendency towards decrease in the number of footslips was seen in the ligand administered group.

Test Example 6: Test for Evaluating Cognitive Function

Figure 6:
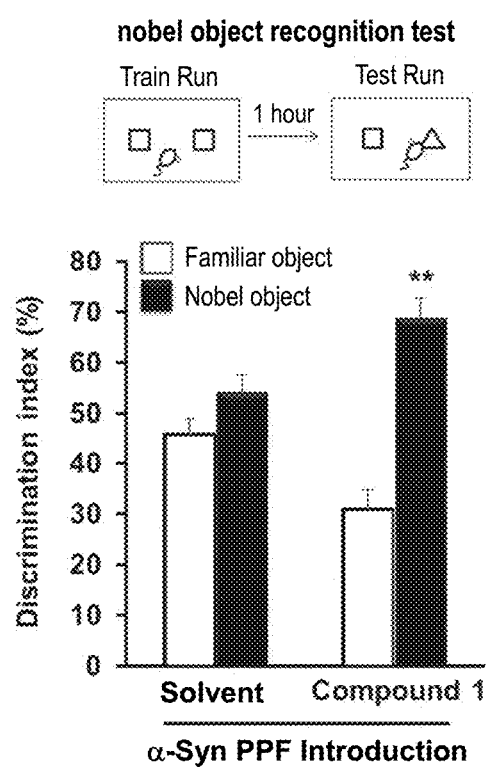
FIG. 6 is a graph showing the result of evaluating the cognitive function by the novel object recognition test in Test Example 6. In the graph showing the result of the novel object recognition test, the vertical axis indicates the ratio of contact of the novel object and the familiar object (Discrimination index (%)). The novel object recognition test showed a significant difference in the contact ratio between the novel object and the familiar object of the ligand administered group, and indicated a tendency towards improvement in the cognitive function.

To an α-Syn PPF-injected mice was administered once every day for 4 weeks a solvent (n=3) or FABP3 ligand (compound of Example 1, 1.0 mg/kg, p.o., n=3), and its cognitive function was evaluated by a novel object recognition test. The novel object recognition test included a train run, in which objects of the same shape were put down for a mouse to memorize, and a test run, in which one object was replaced with a novel object to evaluate the ratio of contact to the two objects. The result is shown in FIG. 6. The significant difference in the novel object recognition test between the ratio of contact of the novel object and the familiar object of the ligand administered group confirmed a tendency towards improvement in the cognitive function.

Figure 7:
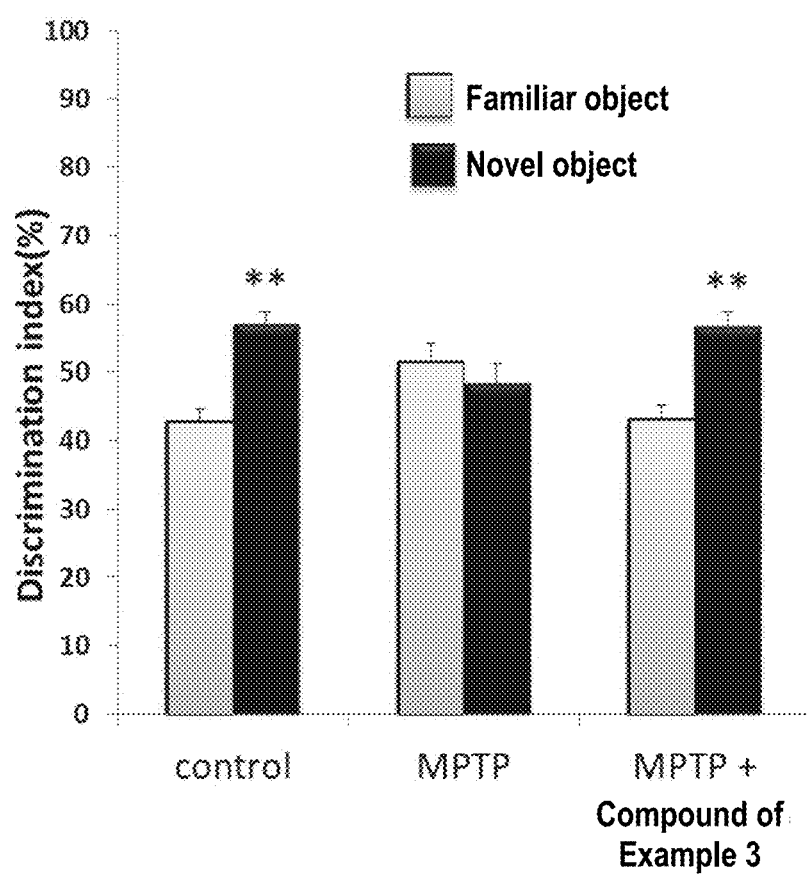
FIG. 7 is a graph showing the result of evaluating the cognitive function by the novel object recognition test in Test Example 7. Whereas the group which received no treatment after MPTP administration demonstrated a cognitive dysfunction, the ligand administered group showed no dysfunction relative to the control group.

Test Example 7: Test for Evaluating Cognitive Function Using Parkinson's Disease Model Animal 1-Methyl-4-phenyl-1,2,3,6-tetrahydropyridine (MPTP, 25 mg/kg, i.p., purchased from Sigma-Aldrich (St Louis, Mo.)), which is a dopamine neurotoxin, was administered once every day for 5 consecutive days to a 10 week old male C57BL6 N mice, to prepare a Parkinson's disease model animal. From 24 hours after the final administration of MPTP, the solvent or FABP3 ligand (compound of Example 3, 1.0 mg/kg, p.o., each group n=7) was administered once every day for 2 weeks. Four weeks after administration of MPTP, at which time cognitive dysfunction was observed, the cognitive function was evaluated by a novel object recognition test. The result is shown in FIG. 7. Whereas cognitive dysfunction was observed in a group which was administered only the solvent after administration of MPTP (control group), such dysfunction was not observed in the ligand administered group.

Figure 8:
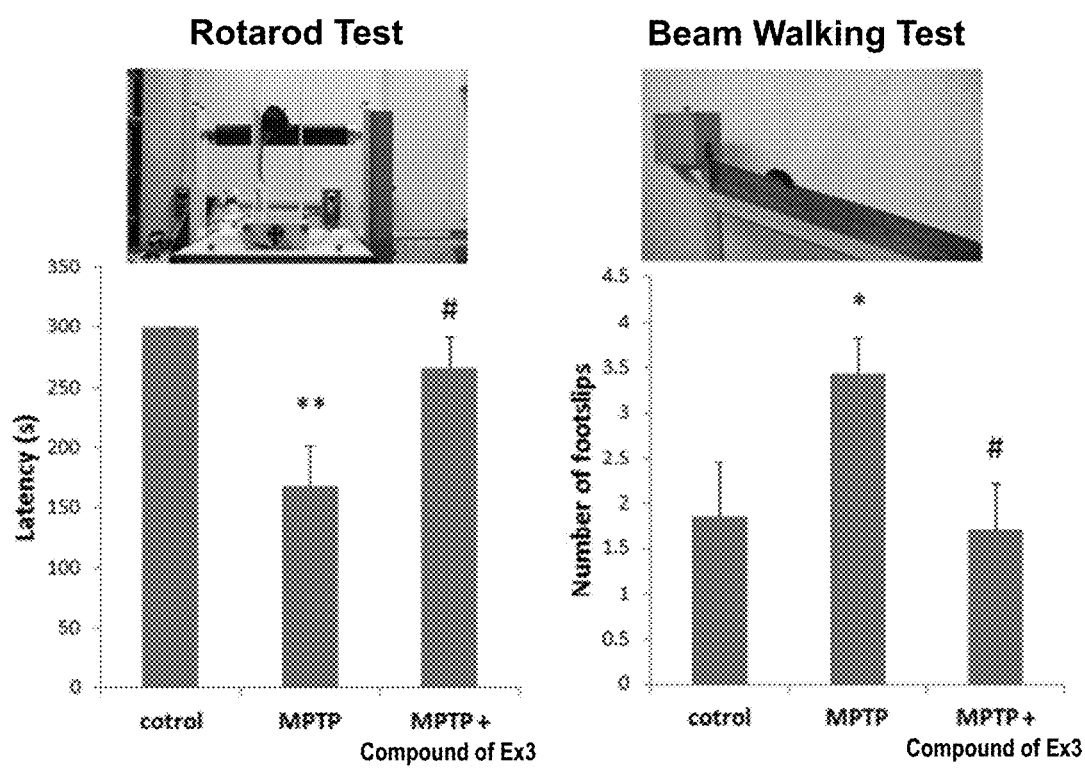
FIG. 8 is a graph showing the result of evaluating the motor function by the rotarod test and the beam walking test in Test Example 8. In both tests, the ligand administered group demonstrated recovery from the motor dysfunction that appeared after MPTP administration.

Test Example 8: Test for Evaluating Motor Function Using a Parkinson's Disease Model Animal From 24 hours after the final administration of MPTP, the solvent or FABP3 ligand (compound of Example 3) (1.0 mg/kg, p.o., each group n=7) was administered once every day for 2 weeks. Three weeks after administration of MPTP, at which time motor dysfunction was observed, the motor function was evaluated by a rotarod test and beam walking test. The result is shown in FIG. 8. In the rotarod test, Latency decreased significantly in a group to which only the solvent was administered (control group), and the ligand administered group recovered fully. In the beam walking test, the number of footslips increased significantly in the control group, and the ligand administered group entirely recovered. It was confirmed in both tests that the ligand administered group was fully recovered from the motor dysfunction that developed after MPTP administration.

Figure 9:
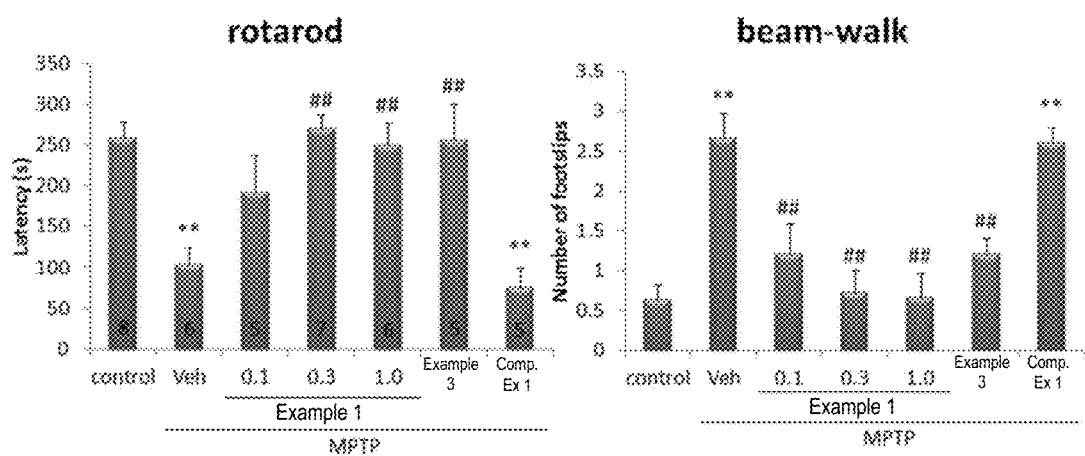
FIG. 9 is a graph showing the result of evaluating the motor function by the rotarod test and beam walking test in Test Example 9. The number shown in each bar in the graph of the rotarod test result stands for n of each group. In both tests, the ligand administered groups were confirmed as recovering from the motor dysfunction which appeared after MPTP administration.

Test Example 9: Test for Evaluating Motor Function Using a Parkinson's Disease Model Animal MPTP (25 mg/kg, i.p.) was administered once every day for 5 consecutive days to a 10 week old male C57BL6 N mice to prepare a Parkinson's disease model mice. From 24 hours after the final administration of MPTP, a solvent (n=6), FABP3 ligand (compound of Example 1, 0.1 mg/kg (n=5), 0.5 mg/kg (n=7), or 1.0 mg/kg (n=6), p.o.), FABP3 ligand (compound of Example 3, 1.0 mg/kg, p.o.) and non-FABP3 ligand (compound of Comparative Example 1, 1.0 mg/kg, p.o.) were administered once every day. Three weeks after administration of MPTP, at which time motor dysfunction was observed, the motor function was evaluated by a rotarod test and beam walking test. The result is shown in FIG. 9. In the rotarod test, the Latency decreased in the group to which only the solvent (control group) was administered, while the Latency improved significantly by administration of the compounds of Examples 1 or 3. However, no improvement was seen for Comparative Example 1. In the beam walking test, the number of footslips increased significantly by MPTP administration, but improved significantly in the compound of Examples 1 or 3, and did not improve for the compound of Comparative Example 1. In other words, whereas no effect was confirmed in the group to which the compound of Comparative Example 1 was administered, a significant effect was confirmed in the groups to which the compounds of Examples 1 and 3 were administered.

Figure 10:
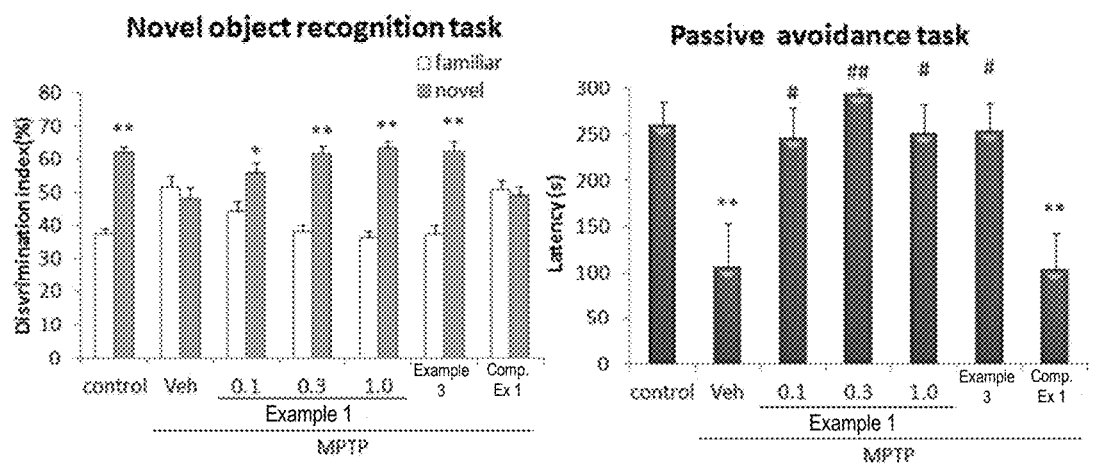
FIG. 10 is a graph showing the result of evaluating the cognitive function by a novel object recognition test and the passive avoidance test in Test Example 9. Whereas the group which received no treatment after MPTP administration demonstrated a cognitive dysfunction, the ligand administered groups showed no dysfunction relative to the control group. The vertical axis of the graph showing the passive avoidance test indicates the time (sec.) it took a mouse to enter the dark room when it is put back in the bright room 24 hours after the test run, in which the mouse was subjected to electric shock when it entered the dark room after being put in a bright room (Latency). In both tests, no effect was confirmed in the group, to which the compound of Comparative Example 1 was administered, but a significant effect was confirmed in the groups, to which the compounds of Examples 1 and 3 were administered.

Test Example 10: Test for Evaluating Cognitive Function Using a Parkinson's Disease Model Animal MPTP (25 mg/kg, i.p.) was administered once every day for 5 consecutive days to a 10 week old male C57BL6 N mice to prepare a Parkinson's disease model mice. From 24 hours after the final administration of MPTP, a solvent (n=6), FABP3 ligand (compound of Example 1, 0.1 mg/kg (n=5), 0.5 mg/kg (n=7), or 1.0 mg/kg (n=6), p.o.), FABP3 ligand (compound of Example 3, 1.0 mg/kg, p.o.) and non-FABP3 ligand (compound of Comparative Example 1, 1.0 mg/kg, p.o.) were administered once every day. Four weeks after administration of MPTP, at which time cognitive dysfunction was observed, the cognitive function was evaluated by a novel object recognition test and a passive avoidance test. The passive avoidance test was performed by putting a mouse in a light room and applying electric shock (0.3 mA, 2 second) on the mouse when it entered the dark room in the train run. Twenty four hours later, the mouse was put in the light room again, and the time until the mouse entered the dark room was measured. The result is shown in FIG. 10.

Whereas no effect was confirmed in the group to which the compound of Comparative Example 1 was administered, the groups to which the compounds of Examples 1 and 3 were administered demonstrated significant effects.

Figure 11:
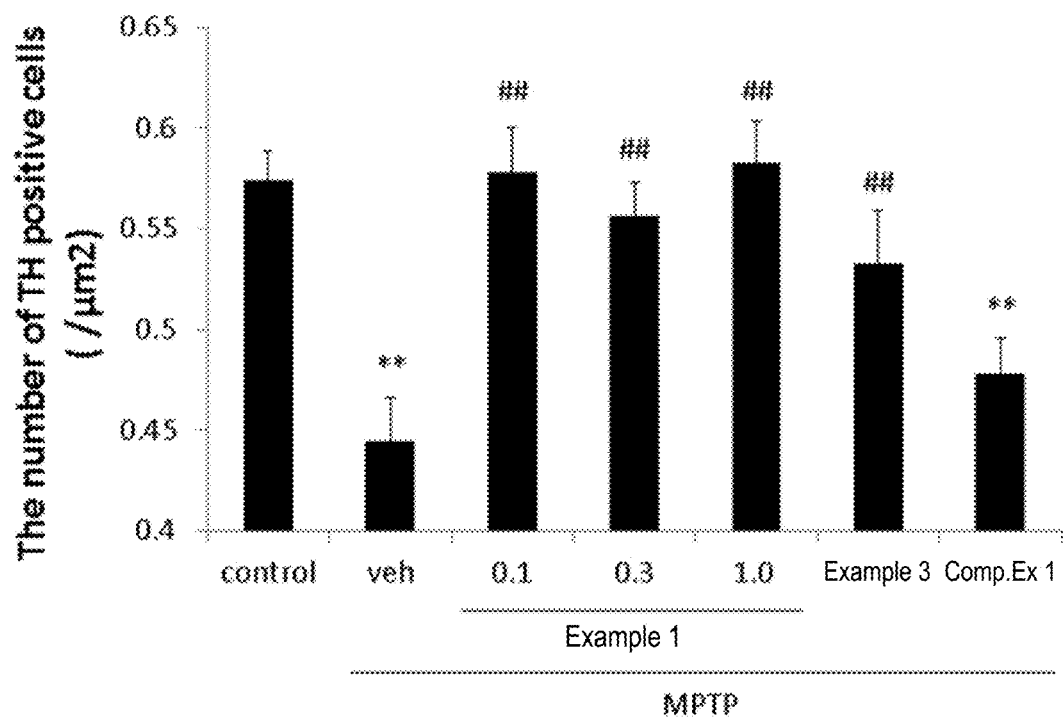
FIG. 11 is a graph showing the result of a test evaluating the protection of dopamine neurons using a Parkinson's disease model animal in Test Example 11.

Test Example 11: Test for Evaluating Dopamine Neuroprotection Using a Parkinson's Disease Model Animal MPTP (25 mg/kg, i.p.) was administered once every day for 5 consecutive days to a 10 week old male C57BL6 N mice to prepare a Parkinson's disease model mice. From 24 hours after the final administration of MPTP, a solvent (n=6), FABP3 ligand (compound of Example 1, 0.1 mg/kg (n=5), 0.3 mg/kg (n=6), or 1.0 mg/kg (n=4), p.o.), FABP3 ligand (compound of Example 3, 1.0 mg/kg (n=4), p.o.) and non-FABP3 ligand (compound of Comparative Example 1, 1.0 mg/kg (n=7), p.o.) were administered once every day. Four weeks after MPTP administration, at which time a loss in the dopamine neuron and formation of α-synuclein multimers are observed, the mouse was fixed under perfusion to prepare a brain slice 50 μm thick that includes a substantia nigra region. The brain slice was reacted with an anti-tyrosine hydroxylase (TH) antibody (mouse monoclonal antibody 22941 produced by Immunostar, 1:1000), which is a marker protein of the dopamine neuron, and detected by a fluorescence-labeled secondary antibody (Alexa 594 anti-mouse IgG (produced by Jackson ImmunoResearch, 1:500)) to evaluate the number of positive cells. The result is shown in FIG. 11.

The number of TH positive cells decreased in the group to which only the solvent was administered, while the number of TH positive cells improved significantly by administration of the compounds of Examples 1 and 3, but not by the compound of Comparative Example 1. In other words, whereas no improvement was confirmed in the number of dopamine neurons for the compound of Comparative Example 1, a significant effect was confirmed in the groups administered the compounds of Examples 1 and 3.

Figure 12:
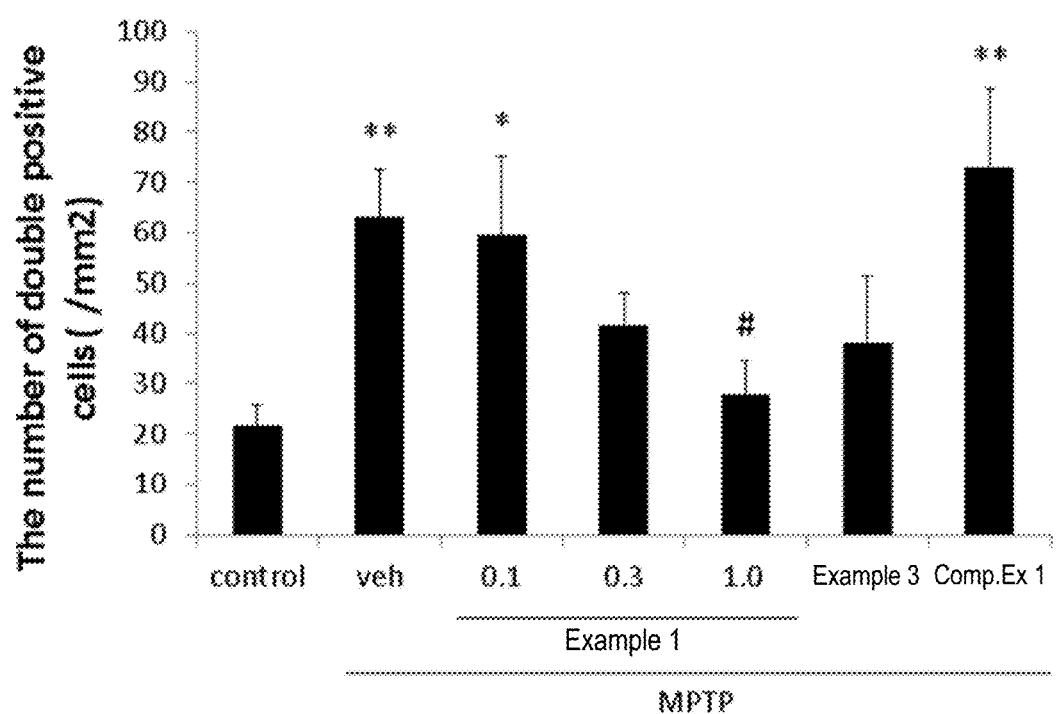
FIG. 12 is a graph showing the result of a test evaluating the suppression of α-synuclein aggregation using a Parkinson's disease model animal in Test Example 12.
Figure 13:
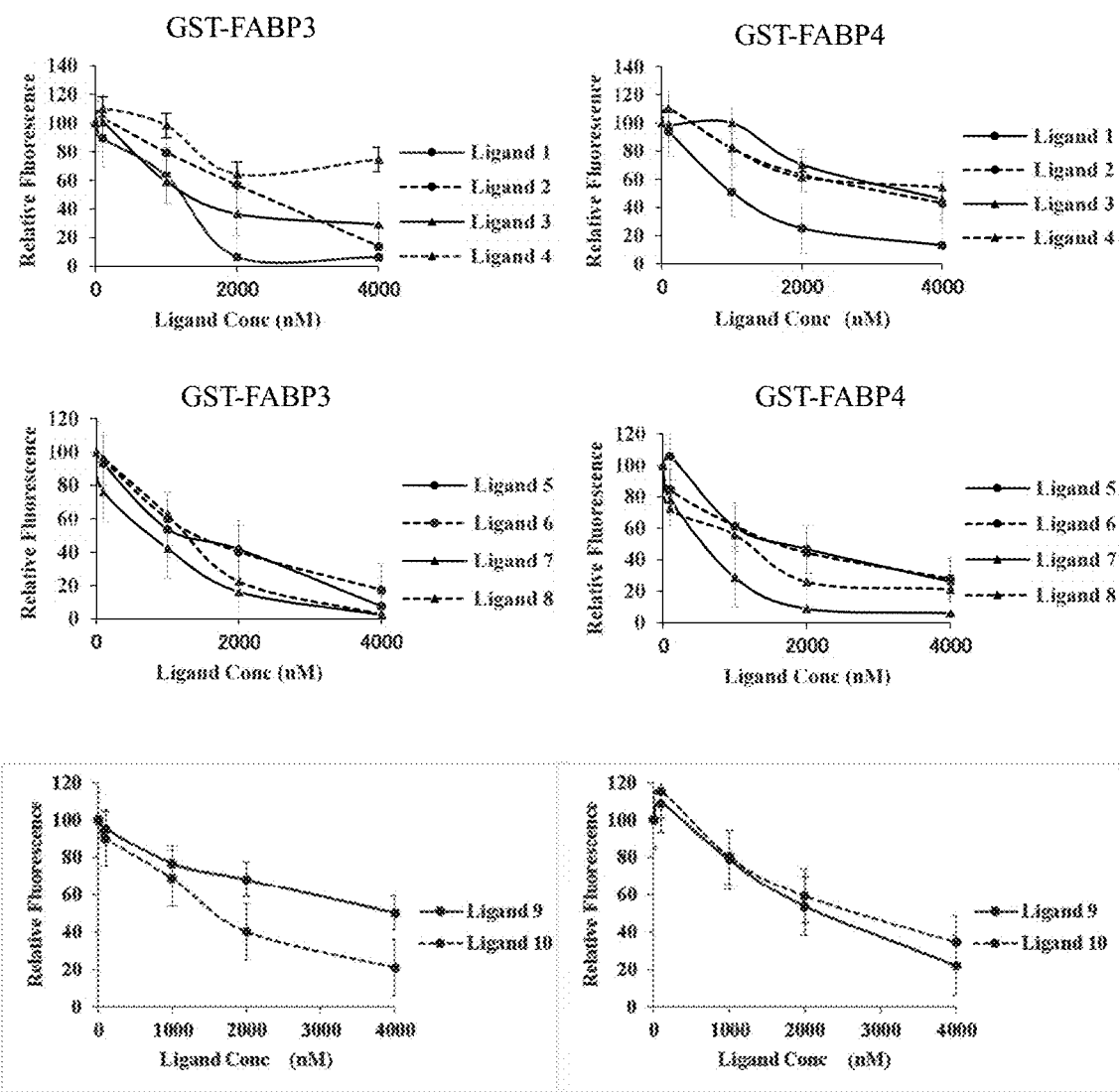
FIG. 13 shows the result of a test for evaluating the affinity of FABP ligand using ANS in Test Example 13.

Test Example 12: Test for Evaluating the Suppression of α-Synuclein Aggregation Using a Parkinson's Disease Model Animal MPTP (25 mg/kg, i.p.) was administered once every day for 5 consecutive days to a 10 week old male C57BL6 N mice to prepare a Parkinson's disease model mice. From 24 hours after the final administration of MPTP, a solvent (n=6), FABP3 ligand (compound of Example 1, 0.1 mg/kg (n=5), 0.3 mg/kg (n=6), or 1.0 mg/kg (n=4), p.o.), FABP3 ligand (compound of Example 3, 1.0 mg/kg (n=4), p.o.) and non-FABP3 ligand (compound of Comparative Example 1, 1.0 mg/kg (n=7), p.o.) were administered once every day. Four weeks after MPTP administration, at which time a loss in the dopamine neuron and formation of α-synuclein multimers are observed, a mouse was fixed under perfusion to prepare a brain slice 50 μm thick that includes a substantia nigra region. The brain slice was reacted with an anti-TH antibody (mouse monoclonal antibody 22941 produced by Immunostar, 1:1000) and an anti-α-synuclein antibody (rabbit polyclonal antibody SC-7011-R produced by Santa Cruz, 1:200) and detected by a fluorescence-labeled, secondary antibody (Alexa 488 anti-rabbit IgG (produced by Jackson ImmunoResearch, 1:500)) to evaluate the number of positive cells. The result is shown in FIG. 12.

The number of TH and α-synuclein double positive cells increased in the group to which only the solvent was administered, while the number improved by the compound of Example 1 and showed tendency towards improvement in Example 3. Meanwhile, there was no improvement in the compound of Comparative Example 1. In other words, regarding the number of dopamine neuron cells that show no synuclein aggregation, no improvement effect was observed in the compound of Comparative Example 1, but a significant effect was observed in the groups to which the compounds of Examples 1 and 3 were administered.

Test Example 13: Test for Evaluating Affinity of FABP Ligand Using ANS

After GST-FABP3 and GST-FABP4 were respectively expressed in the *Escherichia coli* [BL21 (DE3) strain], affinity purification was performed using a glutathione column.

GST-FABP3 and GST-FABP4 vectors were cloned by the following method. The mRNA isolated from the heart of a mouse was subjected to reverse transcription to cDNA, then the FABP3 gene (RefSeqID: NM_010174.1) and the FABP4 gene (RefSeqID: NM_024406.2) were amplified by PCR. These cDNA were injected between the BamHI/EcoRI cleavage site of the pGEX-2T vector (GE Healthcare Japan, Tokyo) respectively using the DNA ligation kit (Takara Bio Inc., Kusatsu) and an In-fusion kit (Takara Bio USA, CA, USA).

FIG. 15 shows the base sequence of GST-FABP3 and GST-FABP4, that had been sequenced (GGATTC and GAATTC at the beginning and the end are the restriction sites).

Purification of the GST binding protein was performed using a GST purification kit (Takara Bio USA). After the *Escherichia coli* was recovered by centrifuging, the accessory extraction buffer and aluminum oxide powder were added and the mixture was ground in the mortar. The centrifuged supernatant was added to the accessory glutathione column and left stationary on ice for 30 min. Then, the supernatant in the column was thrown away, and the remaining matter was washed with the extraction buffer, and subsequently subjected to elution using an elution buffer including glutathione. The protein concentration of the elution product was calculated from the absorbance at 280 nm, and used as an ANS assay.

After the 1-anilinonaphthalene-8-sulfonic acid (ANS, final concentration 4 mM, 10 mM $KH_2PO_4$, 40 mM KCl, in a pH 7.4 solution), which binds to FABP protein and exhibits fluorescence, FABP protein (final concentration 0.4 mM), and various ligands at concentrations of 0 nM, 100 nM, 1000 nM, 2000 nM, 4000 nM (final) were incubated for 2 min., the fluorescence of ANS was measured (Ex/Em=355 nm/460 nm). The fluorescence intensity at the respective ligand concentrations was converted to a relative value (%) against the ANS fluorescence intensity under the absence of ligand, then the dissociation constant Kd(nM) was calculated by a nonrecurring analysis using the following equation.

$$F=F_0-\{[1+(P_t+L_t)Ka-[(P_t-L_t)^2Ka^2+2(P_t+L_t)Ka+1]^{1/2}]/[2P_tKa]\}(F_0-F_{max})$$

F: Relative fluorescence intensity at a certain condition (%);
$F_0$: Fluorescence intensity under the absence of ligand (=100);
$P_t$: FABP protein concentration (=400 nM);
$L_t$: Ligand concentration (=100, 1000, 2000, 4000 nM);
Ka: Reciprocal of dissociation constant Kd ($nM^{-1}$);
$F_{max}$*: Relative fluorescence intensity when FABP is fully occupied by ligands.

The result is shown in Table 2. The ligands used as Ligands 1 to 10 were respectively the compounds of Examples 1 to 3, the compound of Comparative Example 1, and the compounds of Examples 10 to 15. The structural formulae thereof are shown below.

[Formula 47]

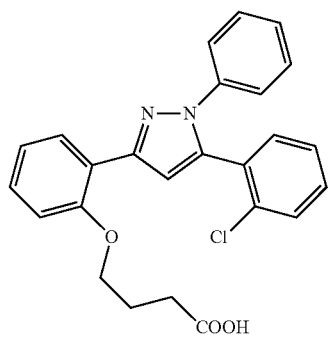

(Ligand 1)

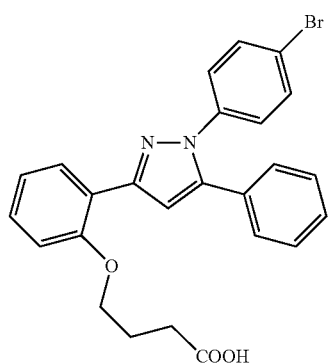

(Ligand 2)

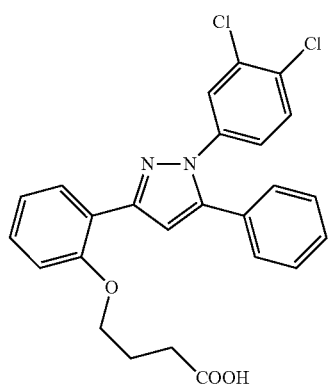

(Ligand 3)

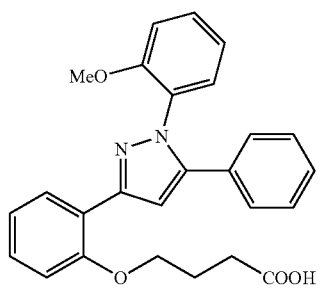

(Ligand 4)

-continued

[Formula 48]

(Ligand 5)
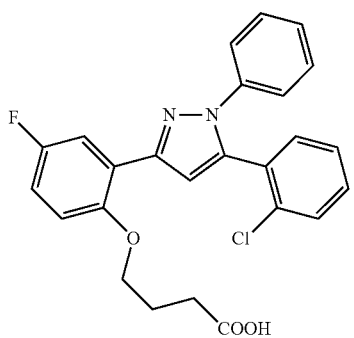

(Ligand 6)
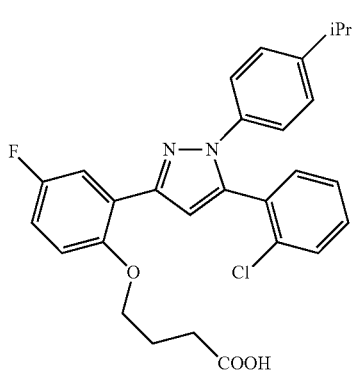

(Ligand 7)
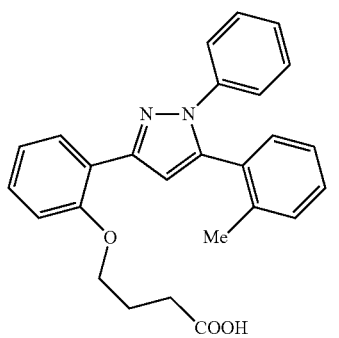

(Ligand 8)
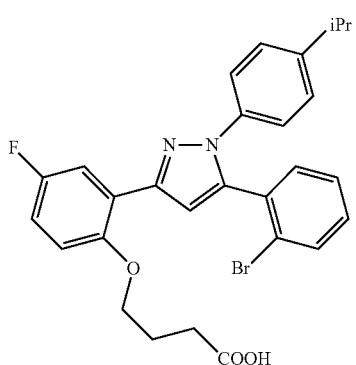

-continued

[Formula 49]

(Ligand 9)
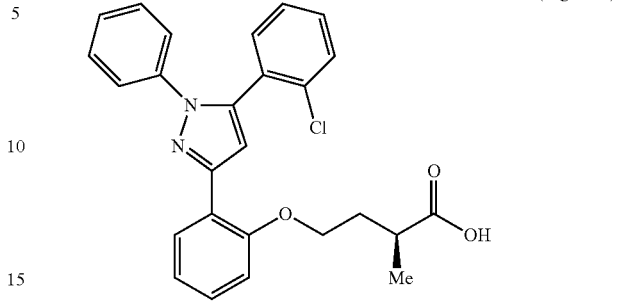

(Ligand 10)
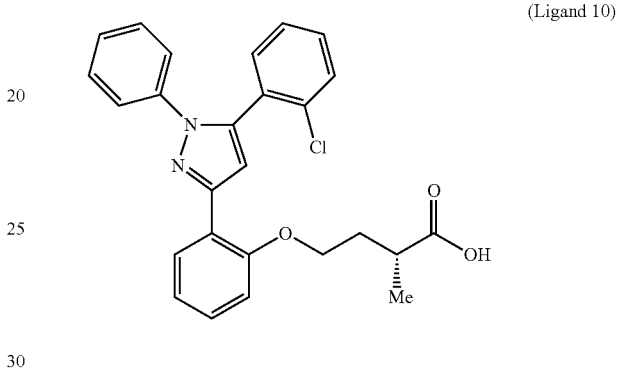

In view of the solubility of the ligand, the relative fluorescence intensities at $L_t=100,000$ nM (excludes Ligands 6 and 8), 20,000 nM (Ligands 6 and 8) were designated as Fmax;

The dissociation constant Kd calculated based on the measurement is shown in the table below.

TABLE 2

| | Kd value of FABP against the ligands | |
|---|---|---|
| | GST-FABP3 | GST-FABP4 |
| Ligand 1 | 386.0 ± 141.2 | 627.2 ± 18.9 |
| Ligand 2 | 1246.5 ± 392.0 | 2329.0 ± 552.6 |
| Ligand 3 | 2216.3 ± 103.9 | 6671.3 ± 1402.7 |
| Ligand 4 | 9624.6 ± 1506.6 | 3816.3 ± 865.3 |
| Ligand 5 | 968.1 ± 338.4 | 1113.0 ± 207.1 |
| Ligand 6 | 1128.2 ± 155.7 | 1417.3 ± 127.3 |
| Ligand 7 | 413.7 ± 128.7 | 388.6 ± 18.3 |
| Ligand 8 | 787.3 ± 170.6 | 401.3 ± 95.8 |
| Ligand 9 | 2845.7 ± 88.3 | 1330.7 ± 118.2 |
| Ligand 10 | 1293 ± 175.7 | 1756.3 ± 90.1 |

The Kd values in the above table are each shown as the average of three measurements±SE.

In the test results shown in the drawings, the marks * and ** respectively indicate significant differences of $p<0.05$ and $p<0.01$ against the control, and # and ## respectively indicate significant differences of $p<0.05$ and $p<0.01$ against the group to which a solvent was administered after MPTP administration.

The invention claimed is:

1. A method for treating synucleinopathy comprising administering to a subject in need thereof an effective amount of a compound represented by formula (Ib) or (Ic):

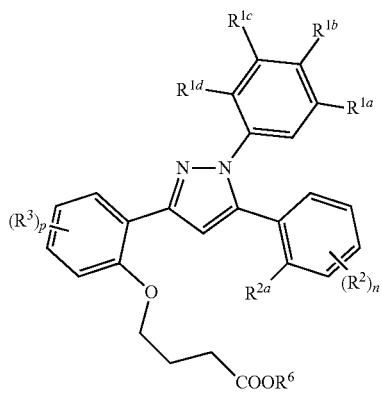
(Ib)

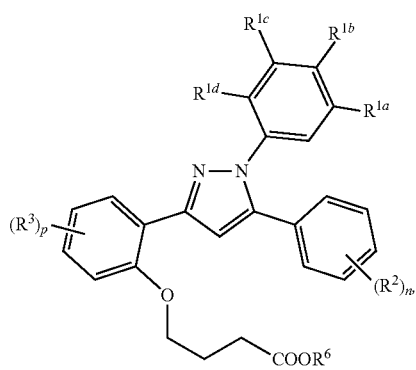
(Ic)

wherein, $R^{1a}$, $R^{1b}$ and $R^{1c}$ are independently selected from a hydrogen atom, $C_{1-6}$ alkyl, $C_{1-6}$ alkoxy, and a halogen atom;

$R^{1d}$ is a hydrogen atom, or a halogen atom;

$R^{2a}$ is selected from $C_{1-6}$ alkyl, and a halogen atom;

$R^{3a}$ is a hydrogen atom or a halogen atom; and $R^2$ is $C_{1-6}$ alkyl, and a halogen atom;
$R^{3b}$ is a halogen atom;
$R^6$ is selected from a hydrogen atom, and $C_{1-6}$ alkyl;
n is an integer selected from 0 to 5;
or a pharmaceutically acceptable salt thereof.

2. The method according to claim 1, wherein n is 0 or 1, p is 0 or 1.

3. The method according to claim 1, wherein $R^{1a}$ and $R^{1b}$ are independently selected from a hydrogen atom, a chlorine atom, a bromine atom, methyl and methoxy.

4. The method according to claim 1, wherein said compound is represented by formula (Ia):

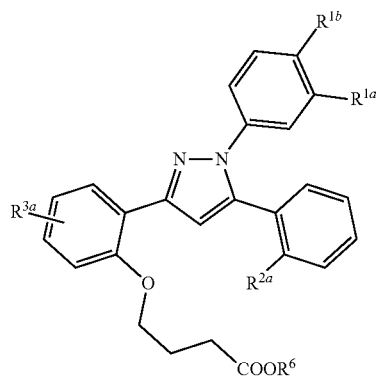

(Ia)

wherein, $R^{1a}$, $R^{1b}$, $R^{2a}$, $R^{3a}$, and $R^6$ are as defined in claim 1,
or a pharmaceutically acceptable salt thereof.

5. The method according to claim 1, wherein $R^6$ is a hydrogen atom.

6. The method according to claim 1, wherein said compound is selected from the following, or a pharmaceutically acceptable salt thereof:

4-(2-(5-(2-chlorophenyl)-1-phenyl-1H-pyrazol-3-yl)phenoxy)butanoic acid;
4-(2-(5-(2-bromophenyl)-1-phenyl-1H-pyrazol-3-yl)phenoxy)butanoic acid;
4-(2-(1,5-diphenyl-1H-pyrazol-3-yl)-4-fluorophenoxy)butanoic acid;
4-(2-(2-chlorophenyl)-1-phenyl-1H-pyrazol-3-yl)-4-fluorophenoxy)butanoic acid;
4-(2-(5-(2-chlorophenyl)-1-(4-isopropylphenyl)-1H-pyrazol-3-yl)-4-fluorophenoxy)butanoic acid;
4-(2-(5-(2-methylphenyl)-1-phenyl-1H-pyrazol-3-yl)-phenoxy)butanoic acid; and
4-(2-(5-(2-bromophenyl)-1-(4-isopropylphenyl)-1H-pyrazol-3-yl)-4-fluorophenoxy)butanoic acid.

7. The method according to claim 1, wherein said synucleinopathy is Parkinson's disease, dementia with Lewy bodies, or multiple system atrophy.

8. The method according to claim 1, wherein the compound is administered orally.

9. A compound represented by formula (Ib):

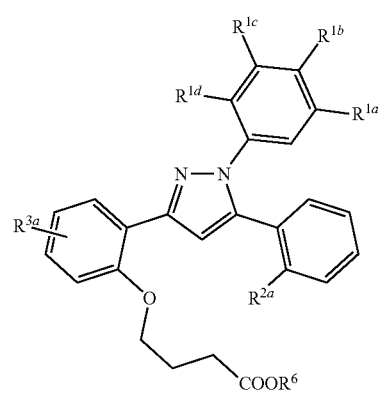

(Ib)

wherein $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;
$R^{2a}$ is selected from $C_{1-6}$ alkyl, and a halogen atom;
$R^{3a}$ is a hydrogen atom or a halogen atom; and
$R^6$ is selected from a hydrogen atom, and $C_{1-6}$ alkyl,
or a pharmaceutically acceptable salt thereof.

10. The compound according to claim 9 or a pharmaceutically acceptable salt thereof, wherein $R^{1d}$ is a hydrogen atom, or a halogen atom.

11. The compound according to claim 9, or a pharmaceutically acceptable salt thereof, wherein $R^{2a}$ is a chlorine atom or a bromine atom.

12. The compound according to claim 9, or a pharmaceutically acceptable salt thereof, wherein $R^{3a}$ is a hydrogen atom or a fluorine atom.

13. A compound represented by formula (Ic):

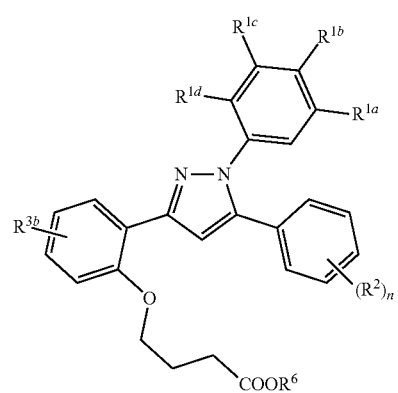

(Ic)

wherein, $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;
$R^2$ is $C_{1-6}$ alkyl, or a halogen atom;
n is an integer selected from 0 to 5;
$R^{1b}$ is a halogen atom;
$R^6$ is selected from a hydrogen atom, and $C_{1-6}$ alkyl,
or a pharmaceutically acceptable salt thereof.

14. The compound according to claim 13 or a pharmaceutically acceptable salt thereof, wherein $R^{1d}$ is a hydrogen atom, or a halogen atom.

15. The compound according to claim 13 or a pharmaceutically acceptable salt thereof, wherein n is 0 or 1.

16. The compound according to claim 13, or a pharmaceutically acceptable salt thereof, wherein $R^{3b}$ is a fluorine atom.

17. A method for treating synucleinopathy comprising administering to a subject an effective amount of the compound represented by formula (Ib):

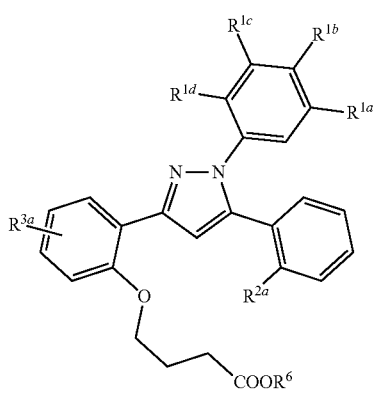

(Ib)

wherein $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;

$R^{2a}$ is selected from $C_{1-6}$ alkyl, and a halogen atom;

$R^{3a}$ is a hydrogen atom or a halogen atom; and $R^6$ is selected from a hydrogen atom, and $C_{1-6}$ alkyl, or a pharmaceutically acceptable salt thereof.

18. The method according to claim 17, wherein said synucleinopathy is Parkinson's disease, dementia with Lewy bodies, or multiple system atrophy.

19. The method according to claim 17, wherein the compound is administered orally.

20. A method for treating synucleinopathy comprising administering to a subject an effective amount of the compound represented by formula (Ic):

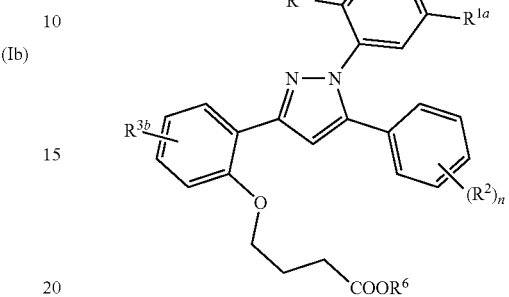

(Ic)

wherein, $R^{1a}$, $R^{1b}$, $R^{1c}$ and $R^{1d}$ are independently selected from a hydrogen atom, $C_{1-6}$ alkyl, $C_{1-6}$ alkoxy, and a halogen atom;

$R^2$ is $C_{1-6}$ alkyl, or a halogen atom;

n is an integer selected from 0 to 5;

$R^{3b}$ is a halogen atom;

$R^6$ is selected from a hydrogen atom, and $C_{1-6}$ alkyl, or a pharmaceutically acceptable salt thereof.

21. The method according to claim 20, wherein said synucleinopathy is Parkinson's disease, dementia with Lewy bodies, or multiple system atrophy.

22. The method according to claim 20, wherein the compound is administered orally.

23. The method according to claim 1, wherein $R^{3b}$ is located at the para-position of the oxygen atom on the benzene ring.

24. The method according to claim 1, wherein $R^{3b}$ is a fluorine atom.

* * * * *

SEQUENCE LISTING

<160> NUMBER OF SEQ ID NOS: 2

<210> SEQ ID NO 1
<211> LENGTH: 414
<212> TYPE: DNA
<213> ORGANISM: mouse

<400> SEQUENCE: 1

```
ggatccatgg cggacgcctt tgtcggtacc tggaagctag tggacagcaa gaattttgat      60
gactacatga agtcactcgg tgtgggcttt gccaccaggc aggtggctag catgaccaag     120
cctactacca tcatcgagaa gaacggggat actatcacca taaagacaca agtaccttc     180 aagaacacag atcaacttt tcagctggga atagagttcg acgaggtgac agcagatgac     240
cggaaggtca agtcactggt gacgctggac ggaggcaaac tcatccatgt gcagaagtgg     300
aacgggcagg agacaacact aactagggag ctagttgacg ggaaactcat cctgactctc     360
actcatggca gtgtggtgag cactcggact tatgagaagg aggcgtgaga attc            414
```

<210> SEQ ID NO 2
<211> LENGTH: 411
<212> TYPE: DNA
<213> ORGANISM: mouse

<400> SEQUENCE: 2

```
ggatccatgt gtgatgcctt tgtgggaacc tggaagcttg tctccagtga aaacttcgat      60
gattacatga agaagtggg agtgggcttt gccacaagga aagtggcagg catggccaag     120
cccaacatga tcatcagcgt aaatggggat ttggtcacca tccggtcaga gagtactttt     180
aaaaacaccg agatttcctt caaactgggc gtggaattcg atgaaatcac cgcagacgac     240
aggaaggtga agagcatcat aaccctagat ggcggggccc tggtgcaggt gcagaagtgg     300
gatggaaagt cgaccacaat aaagagaaaa cgagatggtg acaagctggt ggtggaatgt     360
gttatgaaag gcgtgacttc cacaagagtt tatgaaaggg catgagaatt c                411
```